(12) United States Patent
Armour

(10) Patent No.: US 12,208,102 B2
(45) Date of Patent: Jan. 28, 2025

(54) METHODS OF TREATING CANCER

(71) Applicant: ENDOCYTE, INC., West Lafayette, IN (US)

(72) Inventor: Alison A. Armour, Zionsville, IN (US)

(73) Assignee: ENDOCYTE, INC., West Lafayette, IN (US)

( * ) Notice: Subject to any disclaimer, the term of this patent is extended or adjusted under 35 U.S.C. 154(b) by 886 days.

(21) Appl. No.: 17/047,778

(22) PCT Filed: Apr. 16, 2019

(86) PCT No.: PCT/US2019/027720
§ 371 (c)(1),
(2) Date: Oct. 15, 2020

(87) PCT Pub. No.: WO2019/204335
PCT Pub. Date: Oct. 24, 2019

(65) Prior Publication Data
US 2021/0161911 A1    Jun. 3, 2021

Related U.S. Application Data

(60) Provisional application No. 62/670,442, filed on May 11, 2018, provisional application No. 62/659,016, filed on Apr. 17, 2018.

(51) Int. Cl.
| | | |
|---|---|---|
| A61K 31/555 | (2006.01) | |
| A61K 9/00 | (2006.01) | |
| A61N 5/10 | (2006.01) | |
| A61P 35/00 | (2006.01) | |

(52) U.S. Cl.
CPC .......... *A61K 31/555* (2013.01); *A61K 9/0019* (2013.01); *A61N 5/10* (2013.01); *A61P 35/00* (2018.01)

(58) Field of Classification Search
None
See application file for complete search history.

(56) References Cited

U.S. PATENT DOCUMENTS

| | | |
|---|---|---|
| 4,691,024 A | 9/1987 | Shirahata et al. |
| 4,713,249 A | 12/1987 | Schroder |
| 5,103,018 A | 4/1992 | Motomichi et al. |
| 5,266,333 A | 11/1993 | Cady et al. |
| 5,417,982 A | 5/1995 | Modi |
| 5,418,982 A | 5/1995 | Kishi |
| 5,627,165 A | 5/1997 | Glazier |
| 5,795,877 A | 8/1998 | Jackson et al. |
| 5,863,536 A | 1/1999 | Jackson et al. |
| 5,866,679 A | 2/1999 | DeFeo-Jones et al. |
| 5,902,817 A | 5/1999 | Jackson et al. |
| 5,948,750 A | 9/1999 | Garsky et al. |
| 5,962,237 A | 10/1999 | Ts'o et al. |
| 5,962,521 A | 10/1999 | Jackson et al. |
| 5,968,915 A | 10/1999 | Jackson et al. |
| 5,998,362 A | 12/1999 | Feng et al. |
| 6,054,444 A | 4/2000 | Jackson et al. |
| 6,127,333 A | 10/2000 | Brady et al. |
| 6,174,858 B1 | 1/2001 | Brady et al. |
| 6,177,404 B1 | 1/2001 | DeFeo-Jones et al. |
| 6,232,287 B1 | 5/2001 | Ruoslahti et al. |
| 6,368,598 B1 | 4/2002 | Anthony |
| 6,391,305 B1 | 5/2002 | Feng et al. |
| 6,428,785 B1 | 8/2002 | Gokcen |
| 6,479,470 B1 | 11/2002 | Kozikowski et al. |
| 6,528,499 B1 | 3/2003 | Kozikowski et al. |
| 6,692,724 B1 | 2/2004 | Yang et al. |
| 6,875,886 B2 | 4/2005 | Frangioni |
| 6,946,133 B1 | 9/2005 | Schlom et al. |
| 7,008,765 B1 | 3/2006 | Bussemakers et al. |
| 7,128,893 B2 | 10/2006 | Leamon et al. |
| 7,129,254 B2 | 10/2006 | Berger et al. |
| 7,147,837 B2 | 12/2006 | Lauffer et al. |
| 7,192,586 B2 | 3/2007 | Bander |
| 7,226,577 B2 | 6/2007 | Cappelletti et al. |
| 7,232,805 B2 | 6/2007 | Weinshenker et al. |
| 7,361,338 B2 | 4/2008 | Jakobovits et al. |
| 7,381,745 B2 | 6/2008 | Kozikowski et al. |
| 7,399,460 B2 | 7/2008 | Wedeking et al. |
| 7,408,079 B2 | 8/2008 | Pomper et al. |

(Continued)

FOREIGN PATENT DOCUMENTS

| | | |
|---|---|---|
| AU | 2008289108 | 2/2009 |
| AU | 2014348601 A1 | 5/2016 |
| CA | 2606138 A1 | 10/2007 |
| CA | 2696627 | 2/2009 |
| CN | 1662263 A | 8/2005 |
| CN | 101863924 A | 10/2010 |
| CN | 102014956 A | 4/2011 |
| CN | 103951668 A | 7/2014 |
| CN | 104873982 A | 9/2015 |

(Continued)

OTHER PUBLICATIONS

Hamilou et al. "Treatment of Castration-naive Metastatic Prostate Cancer" European Urology Focus, 2017, vol. 3, No. 6, pp. 518-521. (Year: 2017).*
Vanderpool, Donna; "The Standard of Care" Innovations in Clinical Neuroscience, 2021, vol. 18, No. 7-9, pp. 50-51.*
Lapi, et al., "Assessment of an 18F-Labeled Phosphoramidate Peptidomimetic as a New Prostate-Specific Membrane Antigen-Targeted Imaging Agent for Prostate Cancer," 2009, Journal of Nuclear Medicine, 50(12) pp. 2042-2048.
Leek, et al., "Prostate-specific membrane antigen: evidence for the existence of a second related human gene," 1995, British Journal of Cancer, 72 pp. 583-588.

(Continued)

*Primary Examiner* — Samantha L Shterengarts
*Assistant Examiner* — Jed A Kucharczk
(74) *Attorney, Agent, or Firm* — Barnes & Thornburg LLP

(57) ABSTRACT

The invention described herein pertains to drug delivery conjugates for targeted therapy. The invention described herein relates to methods of treating PSMA expressing cancers with a compound of the formula 1. The invention described herein also relates to methods of treating PSMA-expressing cancers with a compound of the formula 1 inpatients where stable disease results after treatment with the compound of the formula 1.

17 Claims, 1 Drawing Sheet

(56) References Cited

U.S. PATENT DOCUMENTS

| | | |
|---|---|---|
| 7,485,299 B2 | 2/2009 | Afar et al. |
| 7,514,078 B2 | 4/2009 | Bander et al. |
| 7,517,903 B2 | 4/2009 | Chen et al. |
| 7,534,580 B2 | 5/2009 | Reeves et al. |
| 7,601,332 B2 | 10/2009 | Vlahov et al. |
| 7,635,682 B2 | 12/2009 | Denmeade et al. |
| 7,638,122 B2 | 12/2009 | Yu et al. |
| 7,659,395 B2 | 2/2010 | Pajouhesh et al. |
| 7,662,795 B2 | 2/2010 | Rodriguez et al. |
| 7,696,185 B2 | 4/2010 | Berkman |
| 7,713,944 B2 | 5/2010 | Kinberger et al. |
| 7,740,847 B2 | 6/2010 | Allan et al. |
| 7,767,202 B2 | 8/2010 | Pardoll et al. |
| 7,767,803 B2 | 8/2010 | Diener et al. |
| 7,794,929 B2 | 9/2010 | Baylin et al. |
| 7,862,798 B2 | 1/2011 | Leamon et al. |
| 7,872,235 B2 | 1/2011 | Rousso et al. |
| 7,875,586 B2 | 1/2011 | Kovbasnjuk et al. |
| 7,879,981 B2 | 2/2011 | Obata |
| 7,910,594 B2 | 3/2011 | Vlahov et al. |
| RE42,275 E | 4/2011 | Berkman |
| 7,990,533 B2 | 8/2011 | Maier et al. |
| 8,000,773 B2 | 8/2011 | Rousso et al. |
| 8,101,369 B2 | 1/2012 | Nam et al. |
| 8,101,713 B2 | 1/2012 | Cuello et al. |
| 8,105,568 B2 | 1/2012 | Vlahov et al. |
| 8,153,595 B2 | 4/2012 | Chen |
| 8,211,401 B2 | 7/2012 | Babich et al. |
| 8,211,402 B2 | 7/2012 | Babich et al. |
| 8,211,473 B2 | 7/2012 | Troiano et al. |
| 8,211,635 B2 | 7/2012 | Barton |
| 8,227,634 B2 | 7/2012 | Pomper et al. |
| 8,236,330 B2 | 8/2012 | Zale et al. |
| 8,246,968 B2 | 8/2012 | Zale et al. |
| 8,258,111 B2 | 9/2012 | Shen et al. |
| 8,273,363 B2 | 9/2012 | Zale et al. |
| 8,313,128 B2 | 11/2012 | Belyea et al. |
| 8,313,728 B2 | 11/2012 | Leamon et al. |
| 8,388,977 B2 | 3/2013 | Low et al. |
| 8,404,817 B2 | 3/2013 | Sherman et al. |
| 8,414,898 B2 | 4/2013 | Afar et al. |
| 8,445,851 B2 | 5/2013 | Rousso et al. |
| 8,450,290 B2 | 5/2013 | Worm et al. |
| 8,465,725 B2 | 6/2013 | Babich et al. |
| 8,487,128 B2 | 7/2013 | Weissbach et al. |
| 8,487,129 B2 | 7/2013 | Babich et al. |
| 8,507,434 B2 | 8/2013 | Popel et al. |
| 8,557,772 B2 | 10/2013 | Popel et al. |
| 8,562,945 B2 | 10/2013 | Babich et al. |
| 8,603,499 B2 | 12/2013 | Zale et al. |
| 8,603,500 B2 | 12/2013 | Zale et al. |
| 8,603,501 B2 | 12/2013 | Zale et al. |
| 8,606,349 B2 | 12/2013 | Rousso et al. |
| 8,644,910 B2 | 2/2014 | Rousso et al. |
| 8,685,891 B2 | 4/2014 | Muraca |
| 8,703,918 B2 | 4/2014 | Colombatti et al. |
| 8,709,483 B2 | 4/2014 | Farokhzad et al. |
| 8,772,226 B2 | 7/2014 | Denmeade et al. |
| 8,772,459 B2 | 7/2014 | Ho et al. |
| 8,778,305 B2 | 7/2014 | Pomper et al. |
| 8,802,153 B2 | 8/2014 | Cheng et al. |
| 8,816,095 B2 | 8/2014 | Brown et al. |
| 8,834,842 B2 | 9/2014 | Leamon et al. |
| 8,840,865 B2 | 9/2014 | Babich et al. |
| 8,852,630 B2 | 10/2014 | Spiegel et al. |
| 8,859,509 B2 | 10/2014 | Spiegel et al. |
| 8,865,126 B2 | 10/2014 | Leamon et al. |
| 8,865,875 B2 | 10/2014 | Liu et al. |
| 8,877,970 B2 | 11/2014 | Zimmerman et al. |
| 8,901,294 B2 | 12/2014 | Kim et al. |
| 8,907,058 B2 | 12/2014 | Low et al. |
| 8,916,161 B2 | 12/2014 | Buckley |
| 8,916,167 B2 | 12/2014 | Low et al. |
| 8,926,944 B2 | 1/2015 | Babich et al. |
| 8,926,945 B2 | 1/2015 | Port et al. |
| 8,940,871 B2 | 1/2015 | Wu et al. |
| 8,946,388 B2 | 2/2015 | Sahin et al. |
| 8,962,799 B2 | 2/2015 | Babich et al. |
| 8,986,655 B2 | 3/2015 | Weiss et al. |
| 8,987,319 B2 | 3/2015 | Miller |
| 9,044,468 B2 | 6/2015 | Pomper et al. |
| 9,056,841 B2 | 6/2015 | Pomper et al. |
| 9,193,763 B2 | 11/2015 | Low et al. |
| 9,226,981 B2 | 1/2016 | Pomper et al. |
| 9,242,012 B2 | 1/2016 | Ma et al. |
| 9,278,067 B2 | 3/2016 | Boulikas |
| 9,295,727 B2 | 3/2016 | Zale et al. |
| 9,309,193 B2 | 4/2016 | Babich et al. |
| 9,629,918 B2 | 4/2017 | Low et al. |
| 9,636,413 B2 | 5/2017 | Vlahov et al. |
| 9,687,572 B2 | 6/2017 | Babich et al. |
| 9,782,493 B2 | 10/2017 | Vlahov et al. |
| 9,801,956 B2 | 10/2017 | Kularatne et al. |
| 9,808,538 B2 | 11/2017 | Kularatne et al. |
| 9,951,324 B2 | 4/2018 | Low et al. |
| 9,968,691 B2 | 5/2018 | Kularatne et al. |
| 10,046,054 B2 | 8/2018 | Low et al. |
| 10,188,759 B2 | 1/2019 | Vlahov et al. |
| 10,308,606 B2 | 6/2019 | Kularatne et al. |
| 10,363,388 B2 | 7/2019 | Fonseca et al. |
| 10,398,791 B2 | 9/2019 | Eder et al. |
| 10,406,238 B2 | 9/2019 | Low et al. |
| 10,406,240 B2 | 9/2019 | Low et al. |
| 10,456,482 B2 | 10/2019 | Kularatne et al. |
| 10,471,160 B2 | 11/2019 | Eder et al. |
| 10,485,878 B2 | 11/2019 | Low et al. |
| 10,517,956 B2 | 12/2019 | Low et al. |
| 10,517,957 B2 | 12/2019 | Low et al. |
| 10,557,128 B2 | 2/2020 | Low et al. |
| 10,624,969 B2 | 4/2020 | Low et al. |
| 10,624,970 B2 | 4/2020 | Low et al. |
| 10,624,971 B2 | 4/2020 | Low et al. |
| 10,646,581 B2 | 5/2020 | Low et al. |
| 10,688,200 B2 | 6/2020 | Kung et al. |
| 10,828,282 B2 | 11/2020 | Low et al. |
| 10,842,887 B2 | 11/2020 | Kularatne et al. |
| 10,898,596 B2 | 1/2021 | Vlahov et al. |
| 10,912,840 B2 | 2/2021 | Vlahov et al. |
| 11,045,564 B2 | 6/2021 | Eder et al. |
| 11,083,710 B2 | 8/2021 | Low et al. |
| 11,155,800 B2 | 10/2021 | Low et al. |
| 11,298,341 B2 | 4/2022 | Low et al. |
| 11,318,121 B2 | 5/2022 | Low et al. |
| 11,369,590 B2 | 6/2022 | Low et al. |
| 11,484,607 B2 | 11/2022 | Kularatne |
| 11,504,357 B2 | 11/2022 | Low et al. |
| 11,717,514 B2 | 8/2023 | Low et al. |
| 11,931,430 B2 | 3/2024 | Eder et al. |
| 11,951,190 B2 | 4/2024 | Eder et al. |
| 12,091,693 B2 | 9/2024 | Low et al. |
| 2001/0031252 A1 | 10/2001 | Low et al. |
| 2002/0001782 A1 | 1/2002 | Watanabe et al. |
| 2002/0055121 A1 | 5/2002 | Vielkind |
| 2002/0103136 A1 | 8/2002 | Feng |
| 2002/0115596 A1 | 8/2002 | Garsky et al. |
| 2002/0132983 A1 | 9/2002 | Junghans |
| 2003/0035804 A1 | 2/2003 | Anthony |
| 2003/0086900 A1 | 5/2003 | Low et al. |
| 2003/0133927 A1 | 7/2003 | DeFeo-Jones et al. |
| 2003/0138432 A1 | 7/2003 | Glazier |
| 2003/0207808 A1 | 11/2003 | Savitzky et al. |
| 2003/0215456 A1 | 11/2003 | Yao et al. |
| 2003/0220241 A1 | 11/2003 | Defeo-Jones et al. |
| 2003/0232760 A1 | 12/2003 | Garsky et al. |
| 2004/0001846 A1 | 1/2004 | Israeli et al. |
| 2004/0002478 A1 | 1/2004 | Kozikowski et al. |
| 2004/0018203 A1 | 1/2004 | Pastan et al. |
| 2004/0029778 A1 | 2/2004 | Isaacs |
| 2004/0033195 A1 | 2/2004 | Leamon et al. |
| 2004/0052727 A1 | 3/2004 | Dalton et al. |
| 2004/0054190 A1 | 3/2004 | Pomper et al. |
| 2004/0058857 A1 | 3/2004 | Yao |
| 2004/0092890 A1 | 5/2004 | Ash |
| 2004/0110723 A1 | 6/2004 | Frangioni |

(56) References Cited

U.S. PATENT DOCUMENTS

| | | |
|---|---|---|
| 2004/0146516 A1 | 7/2004 | Roben et al. |
| 2004/0213791 A1 | 10/2004 | Bander et al. |
| 2004/0229845 A1 | 11/2004 | Frangioni |
| 2004/0242582 A1 | 12/2004 | Green et al. |
| 2005/0002942 A1 | 1/2005 | Vlahov et al. |
| 2005/0107325 A1 | 5/2005 | Manoharan et al. |
| 2005/0119166 A1 | 6/2005 | Brady et al. |
| 2005/0158780 A1 | 7/2005 | Lupold et al. |
| 2005/0234247 A1 | 10/2005 | Klar et al. |
| 2005/0239138 A1 | 10/2005 | Hess et al. |
| 2005/0239739 A1 | 10/2005 | Matulic-Adamic et al. |
| 2005/0245486 A1 | 11/2005 | Frangioni |
| 2005/0255042 A1 | 11/2005 | Lam et al. |
| 2006/0024317 A1 | 2/2006 | Boyd et al. |
| 2006/0052312 A1 | 3/2006 | Erhardt et al. |
| 2006/0062793 A1 | 3/2006 | Webb et al. |
| 2006/0105975 A1 | 5/2006 | Pendergrast et al. |
| 2006/0106047 A1 | 5/2006 | Jiang et al. |
| 2006/0140871 A1 | 6/2006 | Sillerud |
| 2006/0148718 A1 | 7/2006 | Brady et al. |
| 2006/0155021 A1 | 7/2006 | Lenges et al. |
| 2006/0155146 A1 | 7/2006 | Lenges et al. |
| 2007/0010014 A1 | 1/2007 | Wood et al. |
| 2007/0020177 A1 | 1/2007 | McGill et al. |
| 2007/0020327 A1 | 1/2007 | Fikes et al. |
| 2007/0031326 A1 | 2/2007 | Shirvan et al. |
| 2007/0031438 A1 | 2/2007 | Junghans |
| 2007/0041901 A1 | 2/2007 | Diener et al. |
| 2007/0117153 A1 | 5/2007 | Bieniarz et al. |
| 2007/0128670 A1 | 6/2007 | Klatzmann et al. |
| 2007/0134332 A1 | 6/2007 | Turnell et al. |
| 2007/0142296 A1 | 6/2007 | McBride et al. |
| 2007/0148662 A1 | 6/2007 | Israeli et al. |
| 2007/0160617 A1 | 7/2007 | Ma et al. |
| 2007/0172422 A1 | 7/2007 | Glazier |
| 2007/0179100 A1 | 8/2007 | Manoharan |
| 2007/0219165 A1 | 9/2007 | Berkman |
| 2007/0225213 A1 | 9/2007 | Kosak |
| 2007/0244055 A1 | 10/2007 | Brady et al. |
| 2007/0254316 A1 | 11/2007 | Rodriguez et al. |
| 2007/0254317 A1 | 11/2007 | Busseret-Michel et al. |
| 2008/0008649 A1 | 1/2008 | Cappelletti et al. |
| 2008/0008719 A1 | 1/2008 | Bowdish et al. |
| 2008/0089842 A1 | 4/2008 | Pagel et al. |
| 2008/0089869 A1 | 4/2008 | Denmeade et al. |
| 2008/0114153 A1 | 5/2008 | Steeves et al. |
| 2008/0175789 A1 | 7/2008 | Frangioni |
| 2008/0176821 A1 | 7/2008 | Kozikowski et al. |
| 2008/0193381 A1 | 8/2008 | Babich et al. |
| 2008/0214436 A1 | 9/2008 | Yu et al. |
| 2008/0248052 A1 | 10/2008 | Vlahov et al. |
| 2008/0269105 A1 | 10/2008 | Taft et al. |
| 2008/0311037 A1 | 12/2008 | Heston et al. |
| 2009/0117042 A1 | 5/2009 | Pomper et al. |
| 2009/0123467 A1 | 5/2009 | Bedi et al. |
| 2009/0180951 A1 | 7/2009 | Zimmerman et al. |
| 2009/0214636 A1 | 8/2009 | Low et al. |
| 2009/0247614 A1 | 10/2009 | Manoharan et al. |
| 2009/0258002 A1 | 10/2009 | Barrett et al. |
| 2009/0274625 A1 | 11/2009 | Denmeade et al. |
| 2010/0048490 A1 | 2/2010 | Vlahov et al. |
| 2010/0055735 A1 | 3/2010 | Low et al. |
| 2010/0092496 A1 | 4/2010 | Boyd et al. |
| 2010/0178246 A1 | 7/2010 | Babich et al. |
| 2010/0183509 A1 | 7/2010 | Babich et al. |
| 2010/0183517 A1 | 7/2010 | Berkman |
| 2010/0209343 A1 | 8/2010 | Bander et al. |
| 2010/0234450 A1 | 9/2010 | Schultz et al. |
| 2010/0240701 A1 | 9/2010 | Vlahov et al. |
| 2010/0324008 A1 | 12/2010 | Low et al. |
| 2011/0008253 A1 | 1/2011 | Babich et al. |
| 2011/0027180 A1 | 2/2011 | Magnani |
| 2011/0027274 A1 | 2/2011 | Cheng et al. |
| 2011/0064657 A1 | 3/2011 | Pomper et al. |
| 2011/0142760 A1 | 6/2011 | Pomper et al. |
| 2011/0172254 A1 | 7/2011 | Leamon et al. |
| 2011/0176998 A1 | 7/2011 | Pomper et al. |
| 2011/0200677 A1 | 8/2011 | Chandran et al. |
| 2011/0256157 A1 | 10/2011 | Howard et al. |
| 2011/0288152 A1 | 11/2011 | Low et al. |
| 2012/0009121 A1 | 1/2012 | Pomper et al. |
| 2012/0269726 A1 | 10/2012 | Babich et al. |
| 2012/0276162 A1 | 11/2012 | Zale et al. |
| 2012/0322741 A1 | 12/2012 | Low et al. |
| 2013/0034494 A1 | 2/2013 | Babich et al. |
| 2013/0172406 A1 | 7/2013 | Zale et al. |
| 2013/0315821 A1 | 11/2013 | D'Souza et al. |
| 2013/0336888 A1 | 12/2013 | Babich et al. |
| 2014/0073763 A1 | 3/2014 | Low et al. |
| 2014/0107316 A1 | 4/2014 | Vlahov et al. |
| 2014/0140925 A1 | 5/2014 | Leamon et al. |
| 2014/0154702 A1 | 6/2014 | Parker et al. |
| 2014/0187501 A1 | 7/2014 | Bilodeau et al. |
| 2014/0228541 A1 | 8/2014 | D'Souza et al. |
| 2014/0314864 A1 | 10/2014 | Cheng et al. |
| 2015/0023875 A1 | 1/2015 | Farokhzad et al. |
| 2015/0079001 A1 | 3/2015 | Pomper et al. |
| 2015/0104387 A1 | 4/2015 | Pomper et al. |
| 2015/0110715 A1 | 4/2015 | Eder et al. |
| 2015/0110814 A1 | 4/2015 | Olson et al. |
| 2015/0246144 A1 | 9/2015 | Pomper et al. |
| 2015/0297735 A1 | 10/2015 | Vlahov et al. |
| 2015/0315196 A1 | 11/2015 | Howard |
| 2015/0366968 A1 | 12/2015 | Basilion |
| 2016/0045626 A1 | 2/2016 | McBride et al. |
| 2016/0067341 A1 | 3/2016 | Low et al. |
| 2016/0074526 A1 | 3/2016 | Bilodeau et al. |
| 2016/0114060 A1 | 4/2016 | Pomper et al. |
| 2016/0151508 A1 | 6/2016 | Low et al. |
| 2016/0208021 A1 | 7/2016 | Chang et al. |
| 2016/0220694 A1 | 8/2016 | Vlahov et al. |
| 2016/0228587 A1 | 8/2016 | Eder et al. |
| 2016/0256579 A1 | 9/2016 | Shalom |
| 2016/0287731 A1 | 10/2016 | Vlahov et al. |
| 2016/0361376 A1 | 12/2016 | Vlahov et al. |
| 2016/0361432 A1 | 12/2016 | Vlahov et al. |
| 2016/0361433 A1 | 12/2016 | Vlahov et al. |
| 2017/0226141 A1 | 8/2017 | Slusher et al. |
| 2017/0258923 A1 | 9/2017 | Low et al. |
| 2018/0207298 A1 | 7/2018 | Berkman et al. |
| 2018/0243431 A1 | 8/2018 | Low et al. |
| 2018/0256737 A1 | 9/2018 | Vlahov et al. |
| 2018/0271988 A1 | 9/2018 | Low et al. |
| 2018/0271989 A1 | 9/2018 | Low et al. |
| 2018/0271990 A1 | 9/2018 | Low et al. |
| 2018/0289827 A1 | 10/2018 | Low et al. |
| 2018/0289828 A1 | 10/2018 | Low et al. |
| 2018/0289829 A1 | 10/2018 | Low et al. |
| 2018/0303950 A1 | 10/2018 | Low et al. |
| 2018/0339071 A1 | 11/2018 | Jeong et al. |
| 2018/0346008 A1 | 12/2018 | Nahum et al. |
| 2019/0177345 A1 | 6/2019 | Larsen |
| 2019/0314515 A1 | 10/2019 | Vlahov et al. |
| 2019/0389951 A1 | 12/2019 | Murphy et al. |
| 2020/0155695 A1 | 5/2020 | Low et al. |
| 2020/0155696 A1 | 5/2020 | Low et al. |
| 2020/0188523 A1 | 6/2020 | Low et al. |
| 2020/0261592 A1 | 8/2020 | Low et al. |
| 2020/0297701 A1 | 9/2020 | Low et al. |
| 2021/0077468 A1 | 3/2021 | Low et al. |
| 2021/0154311 A1 | 5/2021 | Vlahov et al. |
| 2021/0154312 A1 | 5/2021 | Vlahov et al. |
| 2021/0161911 A1 | 6/2021 | Armour |
| 2021/0177996 A1 | 6/2021 | Eder et al. |
| 2021/0283279 A1 | 9/2021 | Eder et al. |
| 2021/0322388 A1 | 10/2021 | Low et al. |
| 2021/0323985 A1 | 10/2021 | Leamon et al. |
| 2021/0338641 A1 | 11/2021 | Low et al. |
| 2022/0096445 A1 | 3/2022 | Low et al. |
| 2022/0098564 A1 | 3/2022 | Low et al. |
| 2022/0125957 A1 | 4/2022 | Armour et al. |
| 2022/0125958 A1 | 4/2022 | Vlahov et al. |
| 2022/0220085 A1 | 7/2022 | Vlahov et al. |
| 2022/0265841 A1 | 8/2022 | Vlahov et al. |

(56) References Cited

U.S. PATENT DOCUMENTS

| | | | |
|---|---|---|---|
| 2023/0000836 A1 | 1/2023 | Low et al. | |
| 2023/0098279 A1 | 3/2023 | Leamon et al. | |
| 2023/0346752 A1 | 11/2023 | Low et al. | |

FOREIGN PATENT DOCUMENTS

| | | |
|---|---|---|
| CN | 109134602 A | 1/2019 |
| CN | 111801121 A | 10/2020 |
| DE | 202014008232 U1 | 4/2015 |
| EP | 0116208 B1 | 3/1988 |
| EP | 1177200 B1 | 6/2005 |
| EP | 1472541 B1 | 9/2009 |
| EP | 2136788 B1 | 10/2011 |
| EP | 2373621 A2 | 10/2011 |
| EP | 1999136 B1 | 10/2012 |
| EP | 2436376 B1 | 7/2014 |
| EP | 2759535 A1 | 7/2014 |
| EP | 2240171 B1 | 8/2014 |
| EP | 2170075 B1 | 12/2014 |
| EP | 2823826 A2 | 1/2015 |
| EP | 2097111 B1 | 7/2015 |
| EP | 2938364 A1 | 11/2015 |
| EP | 2993171 A1 | 3/2016 |
| EP | 2706057 B1 | 4/2016 |
| EP | 2389361 B1 | 8/2016 |
| EP | 2318366 B1 | 5/2017 |
| EP | 2408755 B1 | 5/2017 |
| EP | 2644192 B1 | 5/2017 |
| EP | 2644594 B1 | 8/2017 |
| EP | 2648766 B1 | 4/2018 |
| EP | 2942065 B1 | 6/2018 |
| EP | 2921482 B1 | 9/2018 |
| EP | 3038996 B1 | 12/2018 |
| EP | 2187965 B1 | 10/2019 |
| EP | 2958596 B1 | 12/2019 |
| EP | 3388086 B1 | 10/2020 |
| IL | 203998 A0 | 10/2010 |
| JP | 2002506204 A | 2/2002 |
| JP | 2004536034 A | 12/2004 |
| JP | 2005274569 A | 10/2005 |
| JP | 2006501149 A | 1/2006 |
| JP | 2006514961 A | 5/2006 |
| JP | 2006518712 A | 8/2006 |
| JP | 2007521803 A | 8/2007 |
| JP | 2009519209 A | 5/2009 |
| JP | 2010515732 A | 5/2010 |
| JP | 2010518112 A | 5/2010 |
| JP | 2010532754 A | 10/2010 |
| JP | 2010536790 A | 12/2010 |
| JP | 2011132258 A | 7/2011 |
| JP | 2012511023 A | 5/2012 |
| JP | 2014221779 A | 11/2014 |
| JP | 5902237 B2 | 4/2016 |
| JP | 2016153410 A | 8/2016 |
| JP | 2016535013 A | 11/2016 |
| JP | 2017530109 A | 10/2017 |
| JP | 2018058847 A | 4/2018 |
| JP | 2018150350 A | 9/2018 |
| JP | 2019503919 A | 2/2019 |
| JP | 6596479 B2 | 10/2019 |
| JP | 6625690 B2 | 12/2019 |
| JP | 2020073472 A | 5/2020 |
| JP | 2020530007 A | 10/2020 |
| KR | 20030031905 A | 4/2003 |
| PH | 12016500656 A | 6/2016 |
| RU | 2004136995 A | 7/2005 |
| RU | 2404193 C2 | 11/2010 |
| WO | 1988001622 A1 | 3/1988 |
| WO | 1991007418 A1 | 5/1991 |
| WO | 1995033766 A1 | 12/1995 |
| WO | 1999045374 A2 | 9/1999 |
| WO | 2000064911 A1 | 11/2000 |
| WO | 2000066091 A1 | 11/2000 |
| WO | 2001091807 A2 | 12/2001 |
| WO | 2002043773 A2 | 6/2002 |
| WO | 2002062398 A2 | 8/2002 |
| WO | 2002098885 A1 | 12/2002 |
| WO | 2003000201 A2 | 1/2003 |
| WO | 2003060523 A1 | 7/2003 |
| WO | 2003092742 A1 | 11/2003 |
| WO | 2003097105 A1 | 11/2003 |
| WO | 2003097647 A1 | 11/2003 |
| WO | 2004010957 A2 | 2/2004 |
| WO | 2004069159 A2 | 8/2004 |
| WO | 2004069285 A1 | 8/2004 |
| WO | 2005082023 A2 | 9/2005 |
| WO | 2005112919 A2 | 12/2005 |
| WO | 2006012527 A1 | 2/2006 |
| WO | 2006093991 A1 | 9/2006 |
| WO | 2006096754 A2 | 9/2006 |
| WO | 2006104911 A2 | 10/2006 |
| WO | 2006136564 A1 | 12/2006 |
| WO | 2007006041 A2 | 1/2007 |
| WO | 2007022493 A2 | 2/2007 |
| WO | 2007022494 A2 | 2/2007 |
| WO | 2007042504 A2 | 4/2007 |
| WO | 2007106869 A1 | 9/2007 |
| WO | 2008057437 A2 | 5/2008 |
| WO | 2008058192 A2 | 5/2008 |
| WO | 2008088648 A2 | 7/2008 |
| WO | 2008098112 A2 | 8/2008 |
| WO | 2008101231 A2 | 8/2008 |
| WO | 2008121949 A1 | 10/2008 |
| WO | 2009002529 A2 | 12/2008 |
| WO | 2009002993 A1 | 12/2008 |
| WO | 2009026177 A1 | 2/2009 |
| WO | 2009070302 A1 | 6/2009 |
| WO | 2009079024 A1 | 6/2009 |
| WO | 2009082606 A2 | 7/2009 |
| WO | 2009089383 A2 | 7/2009 |
| WO | 2010014933 A2 | 2/2010 |
| WO | 2010065899 A2 | 6/2010 |
| WO | 2010065902 A2 | 6/2010 |
| WO | 2010065906 A2 | 6/2010 |
| WO | 2010108125 A2 | 9/2010 |
| WO | 2011014821 A1 | 2/2011 |
| WO | 2011017249 A1 | 2/2011 |
| WO | 2011106639 A1 | 9/2011 |
| WO | 2011108125 A2 | 9/2011 |
| WO | 2012078534 A1 | 6/2012 |
| WO | 2012166923 A2 | 12/2012 |
| WO | 2012174136 A1 | 12/2012 |
| WO | 2013022797 A1 | 2/2013 |
| WO | 2013028664 A1 | 2/2013 |
| WO | 2013130776 A1 | 9/2013 |
| WO | 2014062697 A2 | 4/2014 |
| WO | 2014078484 A1 | 5/2014 |
| WO | 2014106208 A1 | 7/2014 |
| WO | 2014127365 A1 | 8/2014 |
| WO | 2014134543 A1 | 9/2014 |
| WO | 2015027205 A1 | 2/2015 |
| WO | 2015057250 A1 | 4/2015 |
| WO | WO-2015055318 A1 * | 4/2015 ............ A61K 51/04 |
| WO | 2015171792 A1 | 11/2015 |
| WO | 2016030329 A1 | 3/2016 |
| WO | 2016040179 A1 | 3/2016 |
| WO | 2017116994 A1 | 7/2017 |
| WO | 2018031507 A1 | 2/2018 |
| WO | 2018108287 A1 | 6/2018 |
| WO | 2018187791 A1 | 10/2018 |
| WO | 2018191376 A2 | 10/2018 |
| WO | 2019115684 A1 | 6/2019 |
| WO | 2019165200 | 8/2019 |
| WO | 2019165200 A1 | 8/2019 |
| WO | 2019204335 A1 | 10/2019 |
| WO | 2020061293 A1 | 3/2020 |

OTHER PUBLICATIONS

Lees, et al., "Active surveillance in prostate cancer: patient selection and triggers for intervention," 2012, Current Opinion in Urology, 22(3) pp. 210-215.

(56) References Cited

OTHER PUBLICATIONS

Lesche, et al., "Preclinical evaluation of BAY 1075553, a novel 18F-labelled inhibitor of prostate-specific membrane antigen for PET imaging of prostate cancer," 2014, European Journal of Nuclear Medicine and Molecular Imaging, 41 pp. 89-101.

Liu, et al., "A targeted low molecular weight near-infrared fluorescent probe for prostate cancer," 2010, Bioorganic & Medicinal Chemistry Letters, 20(23) pp. 7124-7126.

Liu, et al., "C-11 Choline PET/CT Imaging for Differentiating Malignant From Benign Prostate Lesions," 2008, Clinical Nuclear Medicine, 33(10) pp. 671-676.

Liu, et al., "Constitutive and Antibody-induced Internalization of Prostate-specific Membrane Antigen," 1998, Cancer Research, 58(18) pp. 4055-4060.

Liu, et al., "Functional prostate-specific membrane antigen is enriched in exosomes from prostate cancer cells," 2014, International Journal of Oncology, 44(3) pp. 918-922.

Liu, et al., "Prolonged androgen deprivation leads to downregulation of androgen receptor and prostate-specific membrane antigen in prostate cancer cells," 2012, International Journal of Oncology, 41(6) pp. 2087-2092.

Liu, et al., "Pseudoirreversible Inhibition of Prostate-Specific Membrane Antigen by Phosphoramidate Peptidomimetics," 2008, Biochemistry, 47(48) pp. 12658-12660.

Liu, et al., "Targeting prostate cancer cells with a multivalent PSMA inhibitor-guided streptavidin conjugate," 2012, Bioorganic & Medicinal Chemistry Letters, 22(12) pp. 3931-3934.

Lord, et al., "18F-Fluorocholine integrated PET/MRI for the initial staging of prostate cancer," 2011, European Journal of Nuclear Medicine and Molecular Imaging, 38 pp. 2288.

Luboldt, et al., "Prostate Carcinoma: Diffusion-weighted Imaging as Potential Alternative to Conventional MR and 11C-Choline PET/CT for Detection of Bone Metastases," 2008, Radiology, 249(3) pp. 1017-1025.

Lutje, et al., "Dual-Modality Image-Guided Surgery of Prostate Cancer with a Radiolabeled Fluorescent Anti-PSMA Monoclonal Antibody," 2014, Journal of Nuclear Medicine, 55(6) pp. 995-1001.

Lutje, et al., "Prospects in Radionuclide Imaging of Prostate Cancer," 2012, The Prostate, 72(11) pp. 1262-1272.

Malik, et al., "One pot radiofluorination of a new potential PSMA ligand [Al18F]NOTA-DUPA-Pep," 2012, Journal of Labelled Compounds and Radiopharmaceuticals, 55(9) pp. 320-325.

Malik, et al., "Radiosynthesis of a new PSMA targeting ligand ([18F]FPy-DUPA-Pep)," 2011, Applied Radiation and Isotopes, 69(7) pp. 1014-1018.

Mannweiler, et al., "Heterogeneity of Prostate-Specific Membrane Antigen (PSMA) Expression in Prostate Carcinoma with Distant Metastasis," 2009, Pathology and Oncology Research, 15(2) pp. 167-172.

Maresca, et al., "Influence of functionalized chelators on affinity and pharmacokinetics of 99mTc(CO)3-labeled small molecules targeting prostate specific membrane antigen (PSMA)," 2010, Journal of Nuclear Medicine, 51(2) pp. 250.

Matthies, et al., "Imaging of prostate cancer metastases with 18F-fluoroacetate using PET/CT," 2004, European Journal of Nuclear Medicine and Molecular Imaging, 31 pp. 797.

Mease, et al., "PET Imaging in Prostate Cancer: Focus on Prostate-Specific Membrane Antigen," 2013, Current Topics in Medicinal Chemistry, 13(8) pp. 951-962.

Meighan, et al., "Recombinant Glutamate Carboxypeptidase II (Prostate Specific Membrane Antigen—PSMA)—Cellular Localization and Bioactivity Analyses," 2003, Journal of Protein Chemistry, 22(4) pp. 317-326.

Meinhardt, et al., "Laparoscopic Sentinel Lymph Node Biopsy for Prostate Cancer: The Relevance of Locations Outside the Extended Dissection Area," 2011, Prostate Cancer, 2012 Article ID 751753, 4 pages.

Melby, E., et at., "Entry of Protein Toxins in Polarized Epithelial Cells," Cancer Research, 1993, 53(8) pp. 1755-1760.

Mertens, et al., "PET with 18F-labelled choline-based tracers for tumour imaging: a review of the literature," 2010, European Journal of Nuclear Medicine and Molecular Imaging, 37 pp. 2188-2193.

Mhawech-Fauceglia, et al., "Prostate-specific membrane antigen (PSMA) protein expression in normal and neoplastic tissues and its sensitivity and specificity in prostate adenocarcinoma: an immunohistochemical study using mutiple tumour tissue microarray technique," 2007, Histopathology, 50(4) pp. 472-483.

Milowsky, et al., "Phase I Trial of Yttrium-90—Labeled Anti-Prostate-Specific Membrane Antigen Monoclonal Antibody J591 for Androgen-Independent Prostate Cancer," 2004, Journal of Clinical Oncology, 22(13) pp. 2522-2531.

Minner, et al., "High Level PSMA Expression Is Associated With Early PSA Recurrence in Surgically Treated Prostate Cancer," 2011, The Prostate, 71(3) pp. 281-288.

Mlcochova, et al., "Mapping of the active site of glutamate carboxypeptidase II by site-directed mutagenesis," 2007, FEBS Journal, 274 pp. 4731-4741.

Moltzahn, et al., "Die ossäre Metastasierung des Prostatakarzinoms," 2012, Urologe, 51 pp. 20-26.

Morris, et al., "11C-acetate PET imaging in prostate cancer," 2007, European Journal of Nuclear Medicine and Molecular Imaging, 34 pp. 181-184.

Murphy, et al., "Current Evaluation of the Tissue Localization and Diagnostic Utility of Prostate Specific Membrane Antigen," 1998, Cancer, 83(11) pp. 2259-2269.

Nedrow-Byers, et al., "A Phosphoramidate-Based Prostate-Specific Membrane Antigen-Targeted SPECT Agent," 2012, The Prostate, 72(8) pp. 904-912.

Oehr et al., "Imaging of prostate cancer," 2007, Current Opinion in Oncology, 19 pp. 259-264.

O'Keefe, et al., "Comparative Analysis of Prostate-Specific Membrane Antigen (PSMA) Versus a Prostate-Specific Membrane Antigen-Like Gene," 2004, The Prostate, 58(2) pp. 200-210.

Omlin, et al., "Androgen- und Östrogen-biosynthesehemmer beim kastrationsresistenten Prostatakarzinom," 2012, Urologe, 51 pp. 8-14.

Osborne, et al., "A Prospective Pilot Study of 89Zr-J591/Prostate Specific Membrane Antigen Positron Emission Tomography in Men with Localized Prostate Cancer Undergoing Radical Prostatectomy," 2014, The Journal of Urology, 19195) pp. 1439-1445.

Oyama, et al., "11C-Acetate PET Imaging of Prostate Cancer," 2002, Journal of Nuclear Medicine, 43(2) pp. 181-186.

Oyama, et al., "11C-Acetate PET Imaging of Prostate Cancer: Detection of Recurrent Disease at PSA Relapse," 2003, Journal of Nuclear Medicine, 44(4) pp. 549-555.

Oyama, et al., "PET Imaging in Prostate Cancer," 2006, Hinyokika Kiyo, 52(6) pp. 503-505.

Parker, et al., "Design, production, and characterization of a single-chain variable fragment (ScFv) derived from the prostate specific membrane antigen (PSMA) monoclonal antibody J591," 2013, Protein Expression and Purification, 89 (2) pp. 136-145.

Pavlicek, et al., "Glutamate Carboxypeptidase II: An Overview of Structural Studies and Their Importance for Structure-Based Drug Design and Deciphering the Reaction Mechanism of the Enzyme," 2012, Current Medicinal Chemistry, 19(9) pp. 1300-1309.

Pavlicek, et al., "Structural characterization of P1'-diversified urea-based inhibitors of glutamate carboxypeptidase II," 2014, Bioorganic & Medicinal Chemistry Letters, 24(10) pp. 2340-2345.

Perner, et al., "Prostate-specific membrane antigen expression as a predictor of prostate cancer progression," 2007, Human Pathology, 38(5) pp. 696-701.

Pillarsetty, et al., "2-18F-Fluoropropionic Acid as a PET Imaging Agent for Prostate Cancer," 2009, Journal of Nuclear Medicine, 50(10) pp. 1709-1714.

Pinto, et al., "Imaging in Prostate Cancer Staging: Present Role and Future Perspectives," 2012, Urology International, 88 pp. 125-136.

Ponde, et al., "18F-Fluoroacetate: A Potential Acetate Analog for Prostate Tumor Imaging—In Vivo Evaluation of 18F-Fluoroacetate Versus 11C-Acetate," 2007, Journal of Nuclear Medicine, 48(3) pp. 420-428.

(56) References Cited

OTHER PUBLICATIONS

James, Shelly, "Urea based rhenium tricarbonyl dipeptide compounds as potential radiopharmaceuticals for PSMA imaging." Poster. INOR258.
Poulsen, et al., "[18F] fluoromethylcholine (FCH) positron emission tomography/computed tomography (PET/CT) for lymph node staging of prostate cancer: a prospective study of 210 patients," 2012, BJU International, 110(11) pp. 1666-1671.
Poulsen, et al., "[18F]-fluorocholine positron-emission/computed tomography for lymph node staging of patients with prostate cancer: preliminary results of a prospective study," 2010, BJU International, 106(5) pp. 639-644.
PCT Search Report and Written Opinion prepared for PCT/US2019/027720, completed May 30, 2019.
Haberkorn, et al., "Mechanistic and high-throughput approaches for the design of molecular imaging probes and targeted therapeutics," 2014, Clinical and Translational Imaging, 2 pp. 33-41.
Haffner, et al., "Prostate-specific membrane antigen expression in the neovasculature of gastric and colorectal cancers," 2009, Human Pathology, 40(12) pp. 1754-1761.
Hain, et al., "Positron emission tomography for urological tumours," 2003, BJU International, 92(2) pp. 159-164.
Hara, et al., "11C-Choline and 2-Deoxy-2-[18F]Fluoro-D-Glucose in Tumor Imaging with Positron Emission Tomography," 2002, Molecular Imaging and Biology, 4(4) pp. 267-273.
Hara, et al., "Development of 18F-Fluoroethylcholine for Cancer Imaging with PET: Synthesis, Biochemistry, and Prostate Cancer Imaging," 2002, Journal of Nuclear Medicine, 43(2) pp. 187-199.
Hara, et al., "PET Imaging of Prostate Cancer Using Carbon-11-Choline," 1998, Journal of Nuclear Medicine, 39(6) pp. 990-995.
Harada, et al., "Preparation of Asymmetric Urea Derivatives that Target Prostate-Specific Membrane Antigen for SPECT Imaging," 2013, Journal of Medicinal Chemistry, 56(20) pp. 7890-7901.
Heidenreich, A., "Immuntherapie beim metastasierten Prostatakarzinom—brauchen wir diese wirklich?," 2012, Urologe, 51 pp. 32-38.
Henry, et al., "A Prostate-Specific Membrane Antigen-Targeted Monoclonal Antibody—Chemotherapeutic Conjugate Designed for the Treatment of Prostate Cancer," 2004, Cancer Research, 64(21) pp. 7995-8001.
Hillier, et al., "123I-MIP-1072, a Small-Molecule Inhibitor of Prostate-Specific Membrane Antigen, Is Effective at Monitoring Tumor Response to Taxane Therapy," 2011, Journal of Nuclear Medicine, 52(7) pp. 1087-1093.
Hillier, et al., "99mTc-Labeled Small-Molecule Inhibitors of Prostate-Specific Membrane Antigen for Molecular Imaging of Prostate Cancer," 2013, Journal of Nuclear Medicine, 54(8) pp. 1369-1376.
Hlouchova, et al., "Biochemical characterization of human glutamate carboxypeptidase III," 2007, Journal of Neurochemistry, 101(3) pp. 682-696.
Hlouchova, et al., "GCPII Variants, Paralogs and Orthologs," 2012, Current Medicinal Chemistry, 19(9) pp. 1316-1322.
Hlouchova, et al., "Structural insight into the evolutionary and pharmacologic homology of glutamate carboxypeptidases II and III," 2009, FEBS Journal, 276)16) pp. 4448-4462.
Ho, et al., "Molecular Imaging, Pharmacokinetics, and Dosimetry of 111In-AMBA in Human Prostate Tumor-Bearing Mice," 2011, Journal of Biomedicine and Biotechnology, Article ID 101497, 8 pages.
Holland, et al., "89Zr-DFO-J591 for ImmunoPET of Prostate-Specific Membrane Antigen Expression In Vivo," 2010, Journal of Nuclear Medicine, 51(8) pp. 1293-1300.
Hong, et al., "Positron emission tomography imaging of prostate cancer," 2010, Amino Acids, 39(1) pp. 11-27.
Hospers, et al., "PET Imaging of Steroid Receptor Expression in Breast and Prostate Cancer," 2008, Current Pharmaceutical Design, 14(28) pp. 3020-3032.
Huang, et al., "Improving the Biodistribution of PSMA-Targeting Tracers With Highly Negatively Charged Linker," 2014, The Prostate, 74(7) pp. 702-713.
Huang, et al., "PSMA-Targeted Stably Linked 'Dendrimer-Glutamate Urea-Methotrexate' as a Prostate Cancer Therapeutic," 2014, Biomacromolecules, 15(3) pp. 915-923.
Humblet, et al., "High-affinity Near-infrared Fluorescent Small-molecule Contrast Agents for In Vivo Imaging of Prostate-specific Membrane Antigen," 2005, Molecular Imaging, 4(4) pp. 448-462.
Humblet, et al., "Multivalent Scaffolds for Affinity Maturation of Small Molecule Cell Surface Binders and Their Application to Prostate Tumor Targeting," 2009, Journal of Medicinal Chemistry, 52(2) pp. 544-550.
Husarik, et al., "Evaluation of [18F]-choline PET/CT for staging and restaging of prostate cancer," 2008, European Journal of Nuclear Medicine and Molecular Imaging, 35 pp. 253-263.
Hwang, et al., "Imaging Prostate Derived Tumors with PET and N-(3-[18F]Fluoropropyl)putrescine," 1990, Nuclear Medicine and Biology, 17(6) pp. 525-532.
Hwang, et al., "N-3-[18F]Fluoropropylputrescine as Potential PET Imaging Agent for Prostate and Prostate Derived Tumors," 1989, Journal of Nuclear Medicine, 30(7) pp. 1205-1210.
Igerc, et al., "The value of 18F-Choline PET/CT in patients with elevated PSA-level and negative prostate needle biopsy for localisation of prostate cancer," 2008, European Journal of Nuclear Medicine and Molecular Imaging, 35(5) pp. 976-983.
Jackson, et al., "Design, Synthesis, and Biological Activity of a Potent Inhibitor of the Neuropeptidase N-Acetylated α-Linked Acidic Dipeptidase," 1996, Journal of Medicinal Chemistry, 39(2) pp. 619-622.
Jadvar, et al., "Glucose Metabolism of Human Prostate Cancer Mouse Xenografts," 2005, Molecular Imaging, 4(2) pp. 91-97.
Jadvar, et al., "Imaging evaluation of prostate cancer with 18F-fluorodeoxyglucose PET/CT: utility and limitations," 2013, European Journal of Nuclear Medicine and Molecular Imaging, 40 (Suppl 1) pp. S5-S10.
Jadvar, et al., "Molecular imaging of prostate cancer with 18F-fluorodeoxyglucose PET," 2009, Nature Reviews Urology, 6(6) pp. 317-323.
Jadvar, et al., "Molecular Imaging of Prostate Cancer: PET Radiotracers," 2012, AJR, 199 pp. 278-291.
Jambor, et al., "Functional Imaging of Localized Prostate Cancer Aggressiveness Using 11C-Acetate PET/CT and 1H-MR Spectroscopy," 2010, Journal of Nuclear Medicine, 51(11) pp. 1676-1683.
Jemaa, et al., "A Comparison of the Biological Features of Prostate Cancer with (PSA+, PSMA+) Profile according to RKIP," 2013, BioMed Research International, 2013(12) Article ID 409179, 7 pages.
Jemaa, et al., "A novel regulation of PSMA and PSA expression by Q640X Ar in 22Rv1 and LNCaP prostate cancer cells," 2013, Cell Biology International, 37(5) pp. 464-470.
Jemaa, et al., "Cellular distribution and heterogeneity of PSA and PSMA expression in normal, hyperplasia and human prostate cancer," 2013, La Tunisie Medicale, 91(7) pp. 458-463.
Kahn, et al., "111Indium-Capromab Pendetide in the Evaluation of Patients with Residual or Recurrent Prostate Cancer After Radical Prostatectomy," 1998, The Journal of Urology, 159(6) pp. 2041-2047.
Kasperzyk, et al., "Prostate-Specific Membrane Antigen Protein Expression in Tumor Tissue and Risk of Lethal Prostate Cancer," Cancer Epidemiol Biomarkers Prev, 22(12) pp. 2354-2363.
Kasten, et al., "Targeting prostate cancer cells with PSMA inhibitor-guided gold nanoparticles," 2013, Bioorganic & Medicinal Chemistry Letters, 23(2) pp. 565-568.
Kim, et al., "Tribody: Robust Self-Assembled Trimeric Targeting Ligands with High Stability and Significantly Improved Target-Binding Strength," 2013, Biochemistry, 52(41) pp. 7283-7294.
Kinoshita, et al., "Expression of Prostate-Specific Membrane Antigen in Normal and Malignant Human Tissues," 2006, World Journal of Surgery, 30(4) pp. 628-636.
Klotz, L. "Cancer overdiagnosis and overtreatment," 2012, Current Opinion in Urology, 22(3) pp. 203-209.
Klusak, et al., "Reaction Mechanism of Glutamate Carboxypeptidase II Revealed by Mutagenesis, X-ray Crystallography, and Computational Methods," 2009, Biochemistry, 48(19) pp. 4126-4138.

(56) References Cited

OTHER PUBLICATIONS

Kosuri, et al., "Review of Salvage Therapy for Biochemically Recurrent Prostate Cancer: The Role of Imaging and Rationale for Systemic Salvage Targeted Anti-Prostate-SpecificMembrane Antigen Radioimmunotherapy," 2012, Advances in Urology, 2012(6) Article ID 921674, 8 pages.
Kotzerke, et al., "PET for Prostate Cancer Imaging: Still a Quandary or the Ultimate Solution?," 2002, The Journal of Nuclear Medicine, 43(2) pp. 200-202.
Kovar, et al., "Pharmacokinetic and Biodistribution Assessment of a Near Infrared-Labeled PSMA-Specific Small Molecule in Tumor-Bearing Mice," 2014, Prostate Cancer, 2014 Article ID 104248, 10 pages.
Krohn, et al., "[68Ga]PSMA-HBED uptake mimicking lymph node metastasis in coeliac ganglia: an important pitfall in clinical practice," 2015, European Journal of Nuclear Medicine and Molecular Imaging, 42(2) pp. 210-214.
Kularatne, et al., "Design, Synthesis, and Preclinical Evaluation of Prostate-Specific Membrane Antigen Targeted 99mTc-Radioimaging Agents," 2009, Molecular Pharmaceuticals, 6(3) pp. 790-800.
Kuru, et al., "MRT-navigierte stereotaktische Prostatabiopsie," 2012, Urologe, 51 pp. 50-56.
Kwee, et al., "18F-choline PET/CT imaging of RECIST measurable lesions in hormone refractory prostate cancer," 2009, Annals of Nuclear Medicine, 23 pp. 541-548.
Lambert, et al., "Molecular Evolution of the Transferrin Receptor/Glutamate Carboxypeptidase II Family," 2007, Journal of Molecular Evolution, 64(1) pp. 113-128.
Bzdega, et al., "The cloning and characterization of a second brain enzyme with NAAG peptidase activity," 2004, Journal of Neurochemistry, 89(3) pp. 627-635.
Ceci, et al., "11C-Choline PET/CT in patients with hormone-resistant prostate cancer showing biochemical relapse after radical prostatectomy," 2013, European Journal of Nuclear Medicine and Molecular Imaging, 40(2) pp. 149-155.
Chandran, et al., "Characterization of a targeted nanoparticle functionalized with a urea-based inhibitor of prostate-specific membrane antigen (PSMA)," 2008, Cancer Biology & Therapy, 7(6) pp. 974-982.
Chang, et al., "Five Different Anti-Prostate-specific Membrane Antigen (PSMA) Antibodies Confirm PSMA Expression in Tumor-associated Neovasculature," 1999, Cancer Research, 59(13) pp. 3192-3198.
Chang, et al., "The clinical role of prostate-specific membrane antigen (PSMA)," 2002, Urologic Oncology, 7(1) pp. 7-12.
Chen, et al., "2-(3-{1-Carboxy-5-[(6-[18F]Fluoro-Pyridine-3-Carbonyl)-Amino]-Pentyl}-Ureido)-Pentanedioic Acid, [18F]DCFPyL, a PSMA-Based PET Imaging Agent for Prostate Cancer," 2011, Clinical Cancer Research, 17(24) pp. 7645-7653.
Chen, et al., "A low molecular weight PSMA-based fluorescent imaging agent for cancer," 2009, Biochemical and Biophysical Research Communications, 390(3) pp. 624-629.
Chen, et al., "PSMA-Targeted Theranostic Nanoplex for Prostate Cancer Therapy," 2012, ACS Nano, 6(9) pp. 7752-7762.
Chen, et al., "Synthesis and Biological Evaluation of Low Molecular Weight Fluorescent Imaging Agents for the Prostate-Specific Membrane Antigen,"2012, Bioconjugate Chemisty, 23(12) pp. 2377-2385.
Chopra, A., "68Ga-Labeled 2-{3-[5-(7-{1-benzyloxycarbonyl-5-[2-(4,7,10-triscarboxymethyl-1,4,7,10-tetraazacyclododec-1-1)acetylamino]pentylcarbamoyl}-heptanoylamino)-1-carboxypentyl]ureido}pentanedioic acid," 2010, Molecular Imaging and Contrast Agent Database (MICAD), pp. 2004-2013.
Chopra, A., "68Ga-Labeled 2-[3-(1-carboxy-5-{7-[5-carboxy-5-(3-phenyl-2-{3-phenyl-2-[2-(4,7, 10-tris- carboxymethyl-1,4,7, 10-tetraazacyclododec-1-l)acetylamino]propionylamino}propionyla mino)pentylcarbamoyl] heptanoylamino}pentyl)ureido]pe ntanedioic acid," 2010, Molecular Imaging and Contrast Agent Database (MICAD), pp. 2004-2013.

Chuu, et al., "Androgen suppresses proliferation of castrationresistant LNCaP 104-R2 prostate cancer cells through androgen receptor, Skp2, and c-Myc," 2011, Cancer Science, 102(11) pp. 2022-2028.
Cimitan, et al., "[18F]fluorocholine PET/CT imaging for the detection of recurrent prostate cancer at PSA relapse: experience in 100 consecutive patients," 2006, European Journal of Nuclear Medicine and Molecular Imaging, 33 pp. 1387-1398.
ClinicalTrials.gov, "99mTc-MIP-1404 for Imaging Prostate Cancer: Phase I Clinical Study to Assess the Image Quality of a Simplified Kit Formulation Compared to a Multi-step Preparation of 99mTc-MIP-1404," Identifier: NCT01654874, available online at: https://clinicaltrials.gov/ct2/show/NCT01654874.
ClinicalTrials.gov, "A Phase 1 Pilot Study of 99mTc-MIP-1404 SPECT/CT Imaging to Histology in Men With Prostate Cancer," Identifier: NCT01615406, available online at: https://clinicaltrials.gov/ct2/show/NCT01615406.
ClinicalTrials.gov, "A Phase 2 Study With MIP-1404 in Men With High-Risk PC Scheduled for RP and EPLND Compared to Histopathology," Identifier: NCT01667536, available online at: https://clinicaltrials.gov/ct2/show/NCT01667536?id=NCT01667536.
ClinicalTrials.gov, "Pilot Study of 99mTc-MIP-1404 SPECT/CT Imaging in Men With Prostate Cancer Undergoing Prostatectomy and/or Pelvic Lymph Node Dissection," Identifier: NCT01572701, available online at: https://clinicaltrials.gov/ct2/show/NCT01572701.
Colabufo, et al., "PB183, a sigma receptor ligand, as a potential PET probe for the imaging of prostate adenocarcinoma," 2008, Bioorganic & Medicinal Chemistry Letters, 18(6) pp. 1990-1993.
Cunha, et al., "Tissue-specificity of prostate specific antigens: Comparative analysis of transcript levels in prostate and non-prostatic tissues," 2006, Cancer Letters, 236(2) pp. 229-238.
Dahl, et al., "Sarcosine induces increase in HER2/neu expression in androgen-dependent prostate cancer cells," 2011, Molecular Biology Reports, 38 pp. 4237-4243.
De Santis, et al., "Rolle der Chemotherapie beim kastrationsresistenten Prostatakarzinom," 2012, Urologe, 51 pp. 39-43.
Degrado, et al., "Synthesis and Evaluation of 18F-Labeled Choline Analogs as Oncologic PET Tracers," 2001, Journal of Nuclear Medicine, 42(12) pp. 1805-1814.
Degrado, et al., "Synthesis and Evaluation of 18F-labeled Choline as an Oncologic Tracer for Positron Emission Tomography: Initial Findings in Prostate Cancer," 2000, Cancer Research, 61(1) pp. 110-117.
Dimitrakopoulou-Strauss, et al., "PET Imaging of Prostate Cancer with 11C-Acetate," 2003, Nuclear Medicine, 44(4) pp. 556-558.
Dumas, et al., "Molecular Expression of PSMA mRNA and Protein in Primary Renal Tumors," 1999, International Journal of Cancer, 80(6) pp. 799-803.
Eder, et al., "Novel Preclinical and Radiopharmaceutical Aspects of [68Ga]Ga-PSMA-HBED-CC: A New PET Tracer for Imaging of Prostate Cancer," 2014, Pharmaceuticals, 7(7) pp. 779-796.
Eder, et al., "Pharmacokinetic Properties of Peptidic Radiopharmaceuticals: Reduced Uptake of (EH)3-Conjugates in Important Organs," 2013, Nuclear Medicine, 54(8) pp. 1-4.
Eder, et al., "Preclinical Evaluation of a Bispecific Low-Molecular HeterodimerTargeting Both PSMA and GRPR for Improved PET Imaging and Therapy of Prostate Cancer," 2014, The Prostate, 74(6) pp. 659-668.
Eder, et al., "PSMA as a target for radiolabelled small molecules," 2013, European Journal of Nuclear Medicine and Molecular Imaging, 40 pp. 819-823.
Eiber, et al., "68Ga-PSMA PET/MR with multimodality image analysis for primary prostate cancer," 2015, Abdom Imaging, 40(6) pp. 1769-1771.
Elsasser-Beile, et al., "A New Generation of Monoclonal and Recombinant Antibodies Against Cell-Adherent Prostate Specific Membrane Antigen for Diagnostic and Therapeutic Targeting of Prostate Cancer," 2006, The Prostate, 66(13) pp. 1359-1370.
Elsasser-Beile, et al., "PET Imaging of Prostate Cancer Xenografts with a Highly Specific Antibody against the Prostate-Specific Membrane Antigen," 2009, Journal of Nuclear Medicine, 50(4) pp. 606-611.

(56) References Cited

OTHER PUBLICATIONS

Elsasser-Beile, et al., "Targeted Therapies for Prostate Cancer Against the Prostate Specific Membrane Antigen," 2009, Current Drug Targets, 10(2) pp. 118-125.
El-Zaria, et al., "Preparation and evaluation of carborane-derived inhibitors of prostate specific membrane antigen (PSMA)," 2014, Dalton Transactions, 43 pp. 4950-4961.
Emonds, et al., "Do androgens control the uptake of 18F-FDG, 11C-choline and 11C-acetate in human prostate cancer cell lines?," 2011, European Journal of Nuclear Medicine and Molecular Imaging, 38(10) pp. 1842-1853.
Evans, et al., "Noninvasive measurement of androgen receptor signaling with a positron-emitting radiopharmaceutical that targets prostate-specific membrane antigen," 2011, Proceedings of the National Academy of Sciences of the United States of America, 108(23) pp. 9578-9582.
Fair, et al., "Prostate-Specific Membrane Antigen," 1997, The Prostate, 32(2) pp. 140-148.
Fall, et al., "Prostate-Specific Antigen Levels as a Predictor of Lethal Prostate Cancer," 2007, Journal of the National Cancer Institute, 99(7) pp. 526-532.
Fortmuller, et al., "Effective Targeting of Prostate Cancer by Lymphocytes Redirected by a PSMA x CD3 Bispecific Single-Chain Diabody," 2011, The Prostate, 71(6) pp. 588-596.
Fortuin, et al., "Value of PET/CT and MR Lymphography in Treatment of Prostate Cancer Patients With Lymph Node Metastases," 2012, International Journal of Radiation Oncology, Biology, Physics, 84(3) pp. 712-718.
Foss, et al., "GCPII Imaging and Cancer," 2012, Current Medicinal Chemistry, 19(9) pp. 1346-1359.
Franc, et al., "Detection and localization of carcinoma within the prostate using high resolution transrectal gamma imaging (TRGI) of monoclonal antibody directed at prostate specific membrane antigen (PSMA)—Proof of concept and initial imaging results," 2013, European Journal of Radiology, 82(11) pp. 1877-1884.
Frigerio, et al., "A single-chain fragment against prostate specific membrane antigen as a tool to build theranostic reagents for prostate cancer," 2013, European Journal of Cancer, 49(9) pp. 2223-2232.
Ghosh, et al., "Tumor Target Prostate Specific Membrane Antigen (PSMA) and its Regulation in Prostate Cancer," 2004, Journal of Cellular Biochemistry, 91(3) pp. 528-539.
Giovacchini, et al., "Predictive factors of [11C]choline PET/CT in patients with biochemical failure after radical prostatectomy," 2010, European Journal of Nuclear Medicine and Molecular Imaging, 37(2) pp. 301-309.
Goodman Jr., et al., "Interaction of prostate specific membrane antigen with clathrin and the adaptor protein complex-2," 2007, International Journal of Oncology, 31(5) pp. 1199-1203.
"Graham, et al., "Radiofluorinated Derivatives of 2-(Phosphonomethyl)pentanedioic Acid as Inhibitors of Prostate Specific Membrane Antigen (PSMA) for the Imaging of Prostate Cancer," 2012, Journal of Medicinal Chemistry, 55(22) pp. 9510-9520."
Grant, et al., "Prostate Specific Membrane Antigen (PSMA) Regulates Angiogenesis Independently of VEGF during Ocular Neovascularization," PLoS ONE 7(7): e41285.
Gregor, et al., "Induction of autoantibodies to syngeneic prostate-specific membrane antigen by xenogeneic vaccination," 2005, International Journal of Cancer, 116(3) pp. 415-421.
Ahmadzadehfar, H., et al., "Overall survival and response pattern of castration-resistant metastatic prostate cancer to multiple cycles of radioligand therapy using [177Lu] Lu-PSMA-617," European Journal of Nuclear Medicine and Molecular Imaging, 2017, 44(9) pp. 1448-1454.
Brauer, A. et al., "177Lu-PSMA-617 radioligand therapy and outcome in patients with metastasized castration-resistant prostate cancer," European Journal of Nuclear Medicine and Molecular Imaging, 2017, 44(10) pp. 1663-1670.
Rahbar, K. et al., "Delayed response after repeated 177Lu-PSMA-617 radioligand therapy in patients with metatstatic castration resistant prostate cancer," European Journal of Nuclear Medicine and Molecular Imaging, 2017, 45(2) pp. 243-246.
Supplemental European Search Report, prepared for EP Application No. 19789294, mailed Nov. 26, 2021.
Yadav, M.P. et al., "177Lu-DKFZ-PSMA-617 therapy in metastatic castration resistant prostate cancer: safety, efficacy, and quality of life assessment," European Jouranl of Nuclear Medicine and Molecular Imaging, 2016, 44(1) pp. 81-91.
Wiberg, et al., "A comparison of some properties of C=O and C=S bonds," 2011, ARKIVOC, 5 pp. 45-56.
De Santis, et al., "Role of Chemotherapy in Castration Resistant Prostate Cancer," 2012, English translation, Urologe, 51(1) pp. 39-43.
Heidenreich, A., "Immunotherapy for Metastatic Prostate Cancer—Do We Really Need This?," English translation, 2012, Urologe, 51(1) pp. 32-38.
Kuru, et al., "MRI Navigated Stereotactic Prostate Biopsy," English Translation, 2012, Urologe, 51(1) pp. 50-56.
Moltzahn, et al., "Bone Metastasis in Prostate Cancer," English translation, 2012, Urologe, 51(1) pp. 20-26.
Omlin, et al., "Inhibitors of Androgen and Estrogen Biosynthesis in Castration-Resistant Prostate Cancer," English translation, 2012, Urologe, 51(1) pp. 8-14.
Preusser, et al., "Castration-Resistant Prostate Cancer," English translation, 2012, Urologe, 51(1) pp. 27-31.
Reske, "Nuclear Imaging of Prostate Cancer," English translation, 2007, Urologe, 46(11) pp. 1485-1499.
Reske, et al., "Advancement of PET and PET/CT in Prostate Carcinoma," English translation, 2006, Urologe, 45(6) pp. 707-714.
Reske, et al., "PET und PET/CT in Relapsing Prostate Carcinoma," English translation, 2006, Urologe, 45(10) pp. 1240-1250.
Spahn, et al., "How Should Hormone Therapy for Castration-Resistant Prostate Cancer be Continued?," English translation, 2012, Urologe, 51(1) pp. 15-19.
Thalmann, G., "Advanced Prostate Cancer," English translation, 2012, Urologe, 51(1) pp. 7.
Weissbach, L. "Which Components Should 'Living Guidelines' Contain?," English translation, 2012, Urologe, 51(1) pp. 57-59.
Benesova, M., et al., "Linker Modifications of DOTA-conjugated Inhibitors of the Prostate-Specific Membrane Antigen (PSMA)," poster, presented at the European Association of Nuclear Medicine Conference on Oct. 21, 2013.
Divyya, et al., "GCPII modulates oxidative stress and prostate cancer susceptibility through changes in methylation of RASSF1, BNIP3, GSTP1 and Ec-SOD," 2013, Mol Biol Rep, 40 pp. 5541-5550.
DNA Interactive Agents, Chapter 6, pp. 386-485.
Drug Discovery General References pp. 98-184.
Drug Metabolism Chapters 7-8, pp. 486-592.
Enzyme Inhibition, Chapter 5, pp. 286-385.
Enzymes, Chapter 4, pp. 186-285.
European Search Report in EP 18175078.7 dated 2018-09-14.
Meienhofer, et al., "Solid-Phase Synthesis with Attachment of Peptide to Resin through an Amino Acid Side Chain: [8-Lysine]-Vasopressin," 1971, Proceedings of the National Academy of Sciences of the United States of America, 68(5) pp. 1006-1009.
Rong, et al., "Molecular Modeling of the Interaction of Glutamate Carboxypeptidase II with Its Potent NAAG-Based Inhibitors," 2002, Journal of Medicinal Chemistry, 45(19) pp. 4140-4152.
Wu, et al., "A mild deprotection procedure for tert-butyl esters and tert-butyl ethers using ZnBr2 in methylene chloride," 2000, Tetrahedron Letters, 41(16) pp. 2847-2849.
Dusich, et al., "General Approach for the Preparation of Fluorescent PSMA/GCPII Inhibitors," 2006, Abstract. Abstract ID: 470, Poster board space: 29.
Foss, et al., "Synthesis and Validation of a Novel Small-Molecule Fluorescent Probe for PSMA Expression in Human Tumor Neovasculature," 2005, Abstract. Abstract ID: 362.
Cole, A., et al., "Cancer theranostics: the rise of targeted magnetic nanoparticles," 2011, Trends in Biotechnology, 29(7) pp. 323-332.
Radioisotopes in Medicine, from http://www.word-nuclear.org/information-library/non-power-nuclear applications/radioisotopes-research/radioisotopes-in-medicine.aspx, Dec. 28, 2016, pp. 1-20.

(56) References Cited

OTHER PUBLICATIONS

The Chemistry of Oxygen and Sulfur, https://web.archive.org/web/20080625021202/http://chemed.chem.purdue.edu/genchem/topicreview/bp/ch10/group6.php#oxygen (date Jun. 25, 2008) accessed online on May 31, 2019, 21 pages (Year: 2008).
European Search Report in EP 18184296 dated Jan. 23, 2019.
European Search Report in EP 18184296 mailed Feb. 12, 2019.
European Search Report in EP 18203547 mailed Apr. 4, 2019.
Jeong, et al., "Preparation of a Promising Angiogenesis PET Imaging Agent: 68Ga-Labeled c(RGDyK)-Isothiocyanatobenzyl-1,4,7-Triazacyclononane-1,4,7-Triacetic Acid and Feasibility Studies in Mice," 2008, The Journal of Nuclear Medicine, 49(5) pp. 830-836.
McBride, et al., "Radiofluorination using aluminum-fluoride (Al18F)", 2013, EJNMMI Research, 3(36) pp. 1-11.
Armor, et al., "A comparison of 2D and 3D regions within the same patient to derive organ and tissue kinetics," 2012, Journal of Nuclear Medicine, 53(1) pp. 13.
Hillier, et al., "[131] MIP-1466, a small molecule prostate-specific membrane antigen (PSMA) inhibitor for targeted radiotherapy of prostate cancer (PCa)," 2012, Journal of Nuclear Medicine, 53(1) pp. 170.
Kothari, et al., "18F-labeled small molecule inhibitors of prostate specific membrane antigen (PSMA) for PET imaging of prostate cancer," 2012, Journal of Nuclear Medicine, 53(1) pp. 1721.
Kularatne, S., et al., "Comparative Analysis of Folate Derived PET Imaging Agents with [18F]-2-Fluoro-2-deoxy-D-glucose Using Rodent Inflammatory Paw Model," 2013, Molecular Pharmaceutics, 10(8) pp. 3103-3111.
Liu, M., et al., "Synthesis and Biological Evaluation of Diethylenetriamine Pentaacetic acid-Polyethylene Glycol Folate: A new Folate-Derived, 99mTc-Based Radiopharmaceutical," 2005, Bioconjugate Chemistry, 16(5) pp. 1126-1132.
Muller, C., et al., "Synthesis and in Vitro/in Vivo Evaluation of Novel 99mTc(CO)3-Folates," 2006, Bioconjugate Chemistry, 17(3) pp. 797-806.
Viola-Villegas, N., et al., "Targeting Gallium to Cancer Cells through the Folate Receptor," 2008, Drug Target Insights, 3 pp. 13-25.
Viola-Villegas, N., et al., "Targeting the Folate Receptor (FR): Imaging and Cytotoxicity of Rel Conjugates in FR-Overexpressing Cancer Cells," 2008, ChemMedChem, 3(9) pp. 1387-1394.
Zhou, J., "In vivo evaluation of medical device-associated inflammation using macrophage-specific position emission tomography (PET) imaging," 2013, Bioorganic and Medicinal Chemistry Letters, 23(7) pp. 2044-2047.
Foss, C., et al. "Radiolabeled Small-molecule Ligands for Prostate-specific Membrane Antigen: In vivo Imaging in Experimental Models of Prostate Cancer," 2005, Clinical Cancer Research, 11(11) pp. 4022-4028.
Kozikowski, A., et al., "Design of Remarkably Simple, Yet Potent Urea-Based Inhibitors of Glutamate Carbozypeptidase II (NAALADase)," 2001, Journal of Medicinal Chemistry, 44(3) pp. 298-301.
Kozikowski, A., et al., "Synthesis of Urea-Based Inhibitors as Active Site Probes of Glutamate Carboxypeptodase II: Efficacy as Analgesic Agents," 2004, Journal of Medicinal Chemistry, 47(7) pp. 1729-1738.
Larock, R., "Comprehensive Organic Transformations: A Guide to Functional Group Preparations," VCH Publishers, Inc. New York (1989).
Lupold, S., et al., "Identification and Characterization of Nuclease-stabilized RNA Molecules that Bind Human Prostate Cancer Cells via the Prostate-specific Membrane Antigen," 2002, Cancer Research, 62(14) pp. 4029-4033.
Majer, P., et al., "Synthesis and Biological Evaluation of Thiol-Based Inhibitors of Glutamate Carboxypeptidase II: Discovery of an Orally Active GCP II Inhibitor, " 2003, Journal of Medicinal Chemistry, 46(10) pp. 1989-1996.
Martin, P., et al., "A New Access to 2'-O-Alkylated Ribonucleosides and Properties of 2'-O-Alkylated Oligoribonucleotides," 1995, Helvetica Chimica Acta, 78(2) pp. 486-504 and Abstract.
McNamara, J., et al., "Cell Type Specific Delivery of siRNAs with Aptamer-siRNA Chimeras," 2006, Nature Biotechnolgy, 24(8) pp. 1005-1015.
Mesters, J., et al., "Structure of Glutamate Carboxypeptidase II, a Drug Target in Neuronal Damage and Prostate Cancer," 2006, The EMBO Journal, 25(6) pp. 1375-1384.
Olsnes, S., et al., "Immunotoxins-Entry into Cells and Mechanisms of Action," 1989, Immunology Today, 10(9) pp. 291-295.
Paranjpe, P., et al., "Tumor-targeted bioconjugate based delivery of camptothecin: design, synthesis and in vitro evaluation," 2004, ScienceDirect Journal of Controlled Release, 100(2) pp. 275-292.
Pathak, T., et al., "Enzymic Protecting Group Techniques in Organic Synthesis," 2000, Stereoselective Biocatalysis pp. 775-797.
Peltier, H., et al., "The Total Synthesis of Tubulysin D," 2006, Journal of the American Chemical Society, 128(50) pp. 16018-16019.
Ranasinghe, M., et al., "A Facile Synthesis of Unsymmetrical Thiolsulfonates via Sulfonylation of Mercaptans," 1988, Synthetic Communications, 18(3) pp. 227-232.
Roy, J., et al., "DUPA Conjugation of a Cytotoxic Indenoisoquinoline Topoisomerase I Inhibitor for Selective Prostate Cancer Cell Targeting," 2015, Journal of Medicinal Chemistry, 58(7) pp. 3094-3103.
Silverman, R., "The Organic Chemistry of Drug Design and Drug Action," Elsevier Academic Press (2nd Ed. 2003).
Silvola, J., et al., "Al18F-NOTA-Folate Accumulates in Atherosclerotic Plaques and Can be Detected by PET/CT", Poster presented Nov, 7, 2015 in Orlando, FL at the 2015 American Heart Association, Resuscitation Science Symposium (http://newsroom_heart.org/events/scientific-sessions-2015-newsroom-2942760).
Silvola, J., et al.,"Al18F-NOTA-Folate Accumulates in Atherosclerotic Plaques and Can be Detected by PET/CT", Published reference of poster, Nov. 10, 2015, at http://circ.ahajournals.org/content/132/Suppl_3/A18873?cited-by=&legid=circulationaha; 132/Suppl_3/A18873; Circulation, 2015, 132:A18873.
Truffert, J., et al., "Synthesis, Purification, and Characterization of Two Peptide-Oligonucleotide Conjugates as Potential Artificial Nucleases," 1996, Tetrahedron, 52(8) pp. 3005-3016.
Vlahov, I., et al., "Design and regioselective synthesis of a new generation of targeted chemotherapeutics. Part 1: EC145, a folic acid conjugate of desacetylvinblastine monohydrazide," 2006, ScienceDirect, Bioorganic & Medical Chemistry Letters, 16(19) pp. 5093-5096.
Yang, J., et al., "Characterization of the pH of Folate Receptor-Containing Endosomes and the Rate of Hydrolysis of Internalized Acid-Labile Folate-Drug Conjugates," 2007, Journal of Pharmacology and Experimental Therapeutics, 321 (2) pp. 462-468.
Istard Posters, 2012, European Journal of Nuclear Medicine and Molecular Imaging, 39(2) pp. 304-353.
Afshar-Oromieh, et al., "[68Ga]Gallium-labelled PSMA ligand as superior PET tracer for the diagnosis of prostate cancer: comparison with 18F-FECH," 2012, European Journal of Nuclear Medicine and Molecular Imaging, 39 pp. 1085-1086.
Afshar-Oromieh, et al., "Comparison of PET imaging with a 68Ga-labelled PSMA ligand and 18F-choline-based PET/CT for the diagnosis of recurrent prostate cancer," 2014, European Journal of Nuclear Medicine and Molecular Imaging, 41(1) pp. 11-20.
Afshar-Oromieh, et al., "Comparison of PET/CT and PET/MRI hybrid systems using a 68Ga-labelled PSMA ligand for the diagnosis of recurrent prostate cancer: initial experience," 2014, European Journal of Nuclear Medicine and Molecular Imaging, 41(5) pp. 887-897.
Afshar-Oromieh, et al., "PET imaging with a [68Ga]gallium-labelled PSMA ligand for the diagnosis of prostate cancer: biodistribution in humans and first evaluation of tumour lesions," 2013, European Journal of Nuclear Medicine and Molecular Imaging, 40 pp. 486-495.
Afshar-Oromieh, et al., "PET/MRI with a 68Ga-PSMA ligand for the detection of prostate cancer," 2013, European Journal of Nuclear Medicine and Molecular Imaging, 40(10) pp. 1629-1630.

(56) References Cited

OTHER PUBLICATIONS

Afshar-Oromieh, et al., "The diagnostic value of PET/CT imaging with the 68Ga-labelled PSMA ligand HBED-CC in the diagnosis of recurrent prostate cancer," 2015, European Journal of Nuclear Medicine and Molecular Imaging, 42 pp. 197-209.
Aggarwal, et al., "A Dimeric Peptide That Binds Selectively to Prostate-Specific Membrane Antigen and Inhibits its Enzymatic Activity," 2006, Cancer Research, 66(18) pp. 9171-9177.
Alt, et al., "High-Resolution Animal PET Imaging of Prostate Cancer Xenografts with Three Different 64Cu-Labeled Antibodies against Native Cell-Adherent PSMA," 2010, The Prostate, 70(13) pp. 1413-1421.
Ananias, et al., "Expression of the Gastrin-Releasing Peptide Receptor, the Prostate Stem Cell Antigen and the Prostate-Specific Membrane Antigen in Lymph Node and Bone Metastases of Prostate Cancer," 2009, The Prostate, 69(10) pp. 1101-1108.
Anderson, et al., "Substrate specificity of prostate-specific membrane antigen," 2007, Bioorganic & Medicinal Chemistry, 15(21) pp. 6678-6686.
Antunes, et al., "PGC and PSMA in prostate cancer diagnosis: tissue analysis from biopsy samples," 2013, International Brazilian Jurnal of Urology, 39(5) pp. 649-656.
Bacich, et al., "Cloning, expression, genomic localization, and enzymatic activities of the mouse homolog of prostate-specific membrane antigen/NAALADase/folate hydrolase," 2001, Mammalian Genome, 12 pp. 117-123.
Baiz, et al., "Synthesis and Characterization of a Novel Prostate Cancer-Targeted Phosphatidylinositol-3-kinase Inhibitor Prodrug," 2012, Journal of Medicinal Chemistry, 55(18 pp. 8038-8046.
Banerjee, et al., "64Cu-Labeled Inhibitors of Prostate-Specific Membrane Antigen for PET Imaging of Prostate Cancer," 2014, Journal of Medicinal Chemistry, 57(6) pp. 2657-2669.
Banerjee, et al., "68Ga-Labeled Inhibitors of Prostate-Specific Membrane Antigen (PSMA) for Imaging Prostate Cancer," 2010, Journal of Medicinal Chemistry, 53(14) pp. 5333-5341.
Banerjee, et al., "A Modular Strategy to Prepare Multivalent Inhibitors of Prostate-Specific Membrane Antigen (PSMA)," 2011, Oncotarget, 2(12) pp. 1244-1253.
Banerjee, et al., "Effect of Chelators on the Pharmacokinetics of 99mTc-Labeled Imaging Agents for the Prostate-Specific Membrane Antigen (PSMA)," 2013, Journal of Medicinal Chemistry, 6(15)5 pp. 6108-6121.
Barinka, et al., "A high-resolution structure of ligand-free human glutamate carboxypeptidase II," 2007, Acta Crystallographica, 63(3) pp. 150-153.
Barinka, et al., "Interactions between Human Glutamate Carboxypeptidase II and Urea-Based Inhibitors: Structural Characterization," 2008, Journal of Medicinal Chemistry, 51 pp. 7737-7743.
Barinka, et al., "Structural Insight into the Pharmacophore Pocket of Human Glutamate Carboxypeptidase II," 2007, Journal of Medicinal Chemistry, 50(14) pp. 3267-3273.
Barrett, et al., "First-in-Man Evaluation of 2 High-Affinity PSMA-Avid Small Molecules for Imaging Prostate Cancer," 2013, Journal of Nuclear Medicine, 54(3) pp. 380-387.
Beheshti, et al., "Prostate Cancer: Role of SPECT and PET in Imaging Bone Metastases," 2009, Seminars in Nuclear Medicine, 39(6) pp. 396-407.
Belloli, et al., "Characterization of preclinical models of prostate cancer using PET-based molecular imaging," 2009, European Journal of Nuclear Medicine and Molecular Imaging, 36 pp. 1245-1255.
Bostwick, et al., "Prostate Specific Membrane Antigen Expression in Prostatic Intraepithelial Neoplasia and Adenocarcinoma," 1998, Cancer, 82(11) pp. 2256-2261.
Bouchelouche, et al., "'Image and treat': an individualized approach to urological tumors," 2010, Current Opinion in Oncology, 22(3) pp. 274-280.
Bouchelouche, et al., "Imaging Prostate Cancer: An Update on Positron Emission Tomography and Magnetic Resonance Imaging," 2010, Current Urology Reports, 11 pp. 180-190.
Bouchelouche, et al., "PET/CT Imaging and Radioimmunotherapy of Prostate Cancer," 2011, Seminar in Nuclear Medicine, 41(1) pp. 29-44.
Bouchelouche, et al., "Prostate Specific Membrane Antigen—A Target for Imaging and Therapy with Radionuclides," 2010, Discovery Medicine, 9(44) pp. 55-61.
Bouchelouche, K., et al., "Positron emission tomography/computed tomography and radioimmunotherapy of prostate cancer," Current Opinion in Oncology, 21(5) pp. 469-474.
Hofman, M.S., et al., "[177Lu]Lu-PSMA-617 versus cabazitaxel in patients with metastatic castration-resistant prostate cancer (TheraP): a randomised, open-label, phase 2 trial," Published Online at the Lancet, Articles, Feb. 11, 2021, pp. 1-8.
Sartor, O. et al., "Lutetium-177-PSMA-617 for Metastatic Castration-Resistant Prostate Cancer," The New England Journal of Medicine, Jun. 23, 2021, pp. 1-13.
ClinicalTrials.gov, "PSMA-directed endoRadiotherapy of castration reSISTant Prostate Cancer (Resist-PC). A Phase II clincial trial." Clinical Trial Results Website, Study Start Date Jul. 2017, Study Completetion Date Jan. 2020, 24 pages.
Violet, J., et al., "Long-Term Follow-up and Outcomes of Retreatment in an Expanded 50-Patient Single-Center Phase II Prospective Trial of 177Lu-PSMA-617 Theranostics in Metastatic Castration-Resistant Prostate Cancer," Journal of Nuclear Medicine, 2020, 61(6) pp. 857-865.
Kratochwil, C., et al., "[177Lu]Lutetium-labelled PSMA ligand-induced remission in a patient with metastatic prostate cancer," Eur J Nucl Med Mol Imaging, 2015, 42, 987-88.
Lau, J., "Bench to Bedside: Albumin Binders for Improved Cancer Radioligand Therapies," 2019, Bioconjugate Chemistry, 30, pp. 487-502.
Wang, Z., Single Low-Dose Injection of Evans Blue Modified PSMA-617 Radioligand Therapy Eliminates Prostate-Specific Membrane Antigen Positive Tumors, Bioconjugate Chemistry, 2018, 29, pp. 3213-3221.
Kratochwil, C., et al., "PSMA-Targeted Radionuclide Therapy of Metastatic Castration-Resistant Prostate Cancer with 177 Lu-Labeled PSMA-617," The Journal of Nuclear Medicine, Mar. 16, 2016, 57(8) pp. 1170-1176.
Sathekge, M., et al., "225Ac-PSMA-617 in chemotherapy-naive patients with advanced prostate cancer: a pilot study," European Journal of Nuclear Medicine and Molecular Imaging, Springer Berlin Heidelberg, Sep. 19, 2018, 46(1) pp. 129-138.
PCT International Search Report for PCT/US2019/051903, completed Oct. 25, 2019.
PCT International Search Report for PCT/US2021/018447, completed May 6, 2021.
Benesova, M., et al., "Linker Modifications of DOTA-conjugated Inhibitors of the Prostate-Specific Membrane Antigen (PSMA)," abstract, European Journal of Nuclear Medicine and Molecular Imaging, available Oct. 16, 2013, 40, Suppl. 2, S193.
Haseman, M., et al., "Capromab Pendetide Imaging of Prostate Cancer," 2000, Cancer Biotherapy and Radiopharmaceuticals, 15(2) pp. 131-140.
Humblet, V., et al., "An HPLC/mass spectrometry platform for the development of multimodality contrast agents and targeted therapeutics: prostate-specific membrane antigen small molecule derivatives," 2006, Contrast Media and Molecular Imaging, 1(5) pp. 196-211.
Lange, P., "ProstaScint scan for staging prostate cancer," 2001, Urology, 57(3) pp. 402-406.
Larson, S., et al., "Tumor Localization of 16β-18F-Fluoro-5α-Dihydrotestosterone Versus 18F-FDG in Patients with Progressive, Metastatic Prostate Cancer," 2004, Journal of Nuclear Medicine, 45(3) pp. 366-373.
Mease, R., et al., "N-[N-[(S)-1,3-Dicarboxypropyl]Carbamoyl]-4-[18F]Fluorobenzyl-LCysteine, [18F]DCFBC: A New Imaging Probe for Prostate Cancer," 2008, Clinical Cancer Research, 14(10) pp. 3036-3043.
Mier, W., et al., "Conjugation of DOTA Using Isolated Phenolic Active Esters: The Labeling and Biodistribution of Albumin as Blood Pool Marker," 2005, Bioconjugate Chemistry, 16(1) pp. 237-240.

(56) References Cited

OTHER PUBLICATIONS

Nan, F., et al., "Dual Function Glutamate-Related Ligands: Discovery of a Novel, Potent Inhibitor of Glutamate Carboxypeptidase II Possessing mGluR3 Agonist Activity," 2000, Journal of Medicinal Chemistry, 43(5) pp. 772-774.
Pomper, M., et al., "11C-MCG: synthesis, uptake selectivity, and primate PET of a probe for glutamate carboxypeptidase II (NAALADase)," 2002, Molecular Imaging, 1(2) pp. 96-101.
Rosenthal, S., et al., "Utility of Capromab Pendetide (ProstaScint) Imaging in the Management of Prostate Cancer," 2001, Techniques in Urology, 7(1) pp. 27-37.
Schafer, et al., "A dimerized urea-based inhibitor of the prostate-specific membrane antigen for 68Ga-PET imaging of prostate cancer," 2012, EJNMMI Research, 2(1) pp. 23.
Schulke, N., et al., "The homodimer of prostate-specific membrane antigen is a functional target for cancer therapy," 2003, Proceedings of the National Academy of Sciences of the United States of America, 100(22) pp. 12590-12595.
Schuster, D., et al., "Initial Experience with the Radiotracer Anti-1-Amino-3-18F-Fluorocyclobutane-1-Carboxylic Acid with PET/CT in Prostate Carcinoma," 2007, Journal of Nuclear Medicine, 48(1) pp. 56-63.
Tasch, J., et al., "A Unique Folate Hydrolase, Prostate-Specific Membrane Antigen (PSMA): A Target for Immunotherapy?" 2001, Critical Reviews in Immunology, 21(1-3) pp. 249-261.
Tehrani, O., et al., "Tumor Imaging Using 1-(2'-deoxy-2'-18F-Fluoro-β-D-Arabinofuranosyl) Thymine and PET," 2007, Journal of Nuclear Medicine, 48(9) pp. 1436-1441.
Vees, H., et al., "18F-choline and/or 11C-acetate positron emission tomography: detection of residual or progressive subclinical disease at very low prostate-specific antigen values (<1 ng/ml) after radical prostatectomy," 2007, BJU International, 99(6) pp. 1415-1420.
Zhou J., et al., "NAAG Peptidase Inhibitors and Their Potential for Diagnosis and Therapy," 2005, Nature Reviews Drug Discovery, 4(12) pp. 1015-1026.
Zophel, K. and Kotzerke, J., "Is 11C-choline the most appropriate tracer for prostate cancer?" 2004, European Journal of Nuclear Medicine and Molecular Imaging, 31(5) pp. 756-759.
Reske, S., et al., "Imaging Prostate Cancer with 11C-Choline PET/CT," 2006, Journal of Nuclear Medicine, 47(8) pp. 1249-1254.
Rinnab, L., et al., "Evaluation of [11C]-choline positron-emission/computed tomography in patients with increasing prostate-specific antigen levels after primary treatment for prostate cancer," 2007, BJU International, 100(4), pp. 786-793.
Scher, B., et al., "Value of 11C-choline PET and PET/CT in patients with suspected prostate cancer," 2007, European Journal of Nuclear Medicine and Molecular Imaging, 34 pp. 45-53.
Jayaprakash, S., et al. "Design and Synthesis of a PSMA inhibitor-doxorubicin Conjugate for Targeted Prostate Cancer Therapy," 2006, ChemMedChem, 1(3) pp. 299-302.
PCT International Search Report for PCT/US2019/052161, completed Dec. 18, 2019.
James, S., "Urea Based Rhenium Tricarbonyl Dipeptide Compounds as Potential Radiopharmaceuticals for PSMA Imgaging," INOR 258, http://oasys2.confex.com/acs/7219nm/techprogram/P830271.html (2018) (1 page).
Nedrow-Byers, et al., "PSMA-Targeted SPECT Agents: Mode of Binding Effect on In Vitro Performance," 2013, The Prostate, 73(4) pp. 355-362.
Roethke, M., et al. "Potenziale der PET/MRT in der Diagnostik des Prostatakariznoms," 2013, Radiologe, 53(8) pp. 676-681.
PCT International Search Report for PCT/US2016/012653, completed Mar. 11, 2016.
Banerjee, S., et al., "Sequential SPECT and Optical Imaging of Experimental Models of Prostate Cancer with a Dual Modality Inhibitor of the Prostate-Specific Membrane Antigen," 2011, Angewandte Chemie International Edition, 50(39) pp. 9167-9170.
Kaur, G., et al., "Biological evaluation of tubulysin A: a potential anticancer and antiangiogenic natural product," 2006, Biochemical Journal, 396(2) pp. 235-242.

Lu, G., et al., "Synthesis and SAR of 99mTc/Re-labeled small molecule prostate specific membrane antigen inhibitors with novel polar chelates," 2013, Bioorganic and Medicinal Chemistry Letters, 23(5) pp. 1557-1563.
PCT International Search Report for PCT/US2011/026238, completed Apr. 27, 2011.
Kularatne, S., et al., "Synthesis and Biological Analysis of Prostate-Specific Membrane Antigen-Targeted Anticancer Prodrugs," 2010, Journal of Medicinal Chemistry, 53(21) pp. 7767-7777.
Banerjee, S., et al., "Synthesis and Evaluation of Technetium-99m- and Rhenium-Labeled Inhibitors of the Prostate-Specific Membrane Antigen (PSMA)," 2008, Journal of Medicinal Chemistry, 51(15) pp. 4504-4517.
Chen, Y., et al., "Radiohalogenated Prostate-Specific Membrane Antigen (PSMA)-Based Ureas as Imaging Agents for Prostate Cancer," 2008, Journal of Medicinal Chemistry, 51(24), pp. 7933-7943.
Hillier, S., et al., "Preclinical Evaluation of Novel Glutamate-Urea-Lysine Analogues That Target Prostate-Specific Membrane Antigen as Molecular Imaging Pharmaceuticals for Prostate Cancer," 2009, Cancer Research, 69(17) pp. 6932-6940.
Kularatne, S., et al., "Prostate-specific membrane antigen targeted imaging and therapy of prostate cancer using a PSMA inhibitor as a homing ligand," 2009, Molecular Pharmaceutics, 6(3) pp. 780-789.
Maresca, K., et al., "A Series of Halogenated Heterodimeric Inhibitors of Prostate Specific Membrane Antigen (PSMA) as Radiolabeled Probes for Targeting Prostate Cancer," 2009, Journal of Medicinal Chemistry, 52(2) pp. 347-357.
Maresca, K., et al., "Molecular targeting of prostate cancer with small molecule inhibitors of prostate specific membrane antigen (PSMA)," 2007, Journal of Nuclear Medicine, 48 (Supplement 2).
Reddy, J., et al., "PSMA-specific anti-tumor activity of the targeted-tubulysin conjugate, EC1169," American Association for Cancer Research Annual Meeting (Apr. 8, 2013) Poster.
Reddy, J., et al., "PSMA-specific anti-tumor activity of the targeted-tubulysin conjugate, EC1169," American Association for Cancer Research Annual Meeting (Apr. 8, 2013) Presentation Abstract.
Wang, et al., "Prostate-Specific Membrane Antigen Targeted Tubulysin Conjugates for Cancer Therapy," 246th ACS National Meeting and Exposition (Sep. 8, 2013) Poster.
Bennett, V. and Simmons, M., "Analysis of fluorescently labeled substance P analogs: binding, imaging and receptor activation," 2001, BMC Chemical Biology, 1:1. doi: 10.1186/1472-6769-1-1.
Davis, M., et al., "Crystal Structure of Prostate-Specific Membrane Antigen, A Tumor Marker and Peptidase," 2005, Proceedings of the National Academy of Sciences of the United States of America, 102(17) pp. 5981-5986.
Definition of ligand, Random House Kernerman Webster's College Dictionary, downloaded on Jan. 25, 2014 from http://www.thefreedictionary.com/ligand, 1 page.
Eder, M., et al., "68Ga-complex Lipophilicity and the Targeting Property of a Urea-based PSMA Inhibitor for PET Imaging," 2012, Bioconjugate Chemistry, 23(4) pp. 688-697.
Farokhzad, O., et al., "Nanoparticle-Aptamer Bioconjugates: A New Approach for Targeting Prostate Cancer Cells," 2004, Cancer Research, 64(21) pp. 7668-7672.
Gomez-Hens, A. and Aguilar-Caballos, M., "Long Wavelength Fluorophores: New Trends in Their Analytical Use," 2004, Trends in Analytical Chemistry, 23(2), pp. 127-136.
Greene, T., and Wuts, P., "Protective Groups ion Organic Synthesis," 2d edition, John Wiley & Sons, Inc. New York (1991).
Henne, W., et al., "Synthesis and activity of a folate peptide camptothecin prodrug," 2006, ScienceDirect, Bioorganic & Medical Chemistry Letters 16(20) pp. 5350-5355.
Jackson, P. and Slusher, B., "Design of NAALADase Inhibitors: A Novel Neuroprotective Strategy," 2001, Current Medicinal Chemistry, 8(8) pp. 949-957.
Preusser, et al., "Kastrationsresistentes Prostatakarzinom," 2012, Urologe, 51 pp. 27-31.
Pubchem, Compound summary for: CID 58099954, Aug. 19, 2012.

(56) References Cited

OTHER PUBLICATIONS

Rais, et al., "Bioanalytical method for evaluating the pharmacokinetics of the GCP-II inhibitor 2-phosphonomethylpentanedioicacid (2-PMPA)," 2014, Journal of Pharmaceutical and Biomedical Analysis, 88(25) pp. 162-169.
Rajasekaran, et al., "A Novel Cytoplasmic Tail MXXXL Motif Mediates the Internalization of Prostate-specific Membrane Antigen," 2003, Molecular Biology of the Cell, 14(12) pp. 4835-4845.
Reske, et al., "[11C]choline PET/CT imaging in occult local relapse of prostate cancer after radical prostatectomy," 2008, European Journal of Nuclear Medicine and Molecular Imaging, 35 pp. 9-17.
Reske, et al., "[11C]Choline uptake with PET/CT for the initial diagnosis of prostate cancer: relation to PSA levels, tumour stage and anti-androgenic therapy," 2008, European Journal of Nuclear Medicine and Molecular Imaging, 35(9) pp. 1740-1741.
Reske, et al., "Nuklearmedizinische Diagnostik beim Prostatakarzinom," 2007, Urologe, 46 pp. 1485-1499.
Reske, et al., "PET und PET/CT in der Rezidivdiagnostik des Prostatakarzinoms," 2006, Urologe, 45 pp. 1240-1250.
Reske, et al., "Weiterentwicklung der PET und des PET/CT beim Prostatakarzinom," 2006, Urologe, 45 pp. 707-714.
Rinnab, et al., "[11C]Choline PET/CT for Targeted Salvage Lymph Node Dissection in Patients with Biochemical Recurrence after Primary Curative Therapy for Prostate Cancer," 2008, Urology International, 81 pp. 191-197.
Rinnab, et al., "[11C]choline PET/CT in prostate cancer patients with biochemical recurrence after radical prostatectomy," 2009, World Journal of Urology, 27 pp. 619-625.
Rioja, et al., "Role of positron emission tomography in urological oncology," BJU International, 106(11) pp. 1578-1593.
Ristau, et al., "The prostate-specific membrane antigen: Lessons and current clinical implications from 20 years of research," 2014, Urologic Oncology: Seminars and Original Investigations, 32(3) pp. 272-279.
Roethke, et al., "Hybrid Positron Emission Tomography-Magnetic Resonance Imaging with Gallium 68 Prostate-specific Membrane Antigen Tracer: A Next Step for Imaging of Recurrent Prostate Cancer—Preliminary Results," 2013, European Urology, 64(5) pp. 862-864.
Rybalov, et al., "Impact of total Psa, Psa doubling time and PSA velocity on detection rates of 11C-Choline positron emission tomography in recurrent prostate cancer," 2013, World Journal of Urology, 31(2) pp. 319-323.
Sacha, et al., "Expression of Glutamate Carboxypeptidase II in Human Brain," 2007, Neuroscience, 144(4) pp. 1361-1372.
Scattoni, et al., "Detection of Lymph-Node Metastases with Integrated [11C]Choline PET/CT in Patients with PSA Failure after Radical Retropubic Prostatectomy: Results Confirmed by Open Pelvic-Retroperitoneal Lymphadenectomy," 2007, European Urology, 52(2) pp. 423-429.
Scheffel, et al., "PET Imaging of GRP Receptor Expression in Prostate Cancer," 2004, The Journal of Nuclear Medicine, 45(8) pp. 1277-1278.
Scher, et al., "PET/CT imaging of recurrent prostate cancer," 2008, European Journal of Nuclear Medicine and Molecular Imaging, 35 pp. 5-8.
Shvarts, et al., "Positron Emission Tomography in Urologic Oncology," 2002, Cancer Control, 9(4) pp. 335-342.
Silver, et al., "Prostate-specific Membrane Antigen Expression in Normal and Malignant Human Tissues," 1997, Clinical Cancer Research, 3(1) pp. 81-85.
Simone, et al., "What's in a Label? Radioimmunotherapy for Metastatic Prostate Cancer," 2013, Clinical Cancer Research, 19(18) pp. 4908-4910.
Slusher, et al., "Immunocytochemical Localization of the N-Acetyl-Aspartyl-Glutamate (NAAG) Hydrolyzing Enzyme N-Acetylated α-Linked Acidic Dipeptidase (NAALADase)," 1992, The Journal of Comparative Neuorology, 315(2) pp. 217-229.
Slusher, et al., "Selective inhibition of NAALADase, which converts NAAG to glutamate, reduces ischemic brain Injury," 1999, Nature Medicine, 5(12) pp. 1396-1402.
Soloviev, et al., "PET imaging with 11C-acetate in prostate cancer: a biochemical, radiochemical and clinical perspective," 2008, European Journal of Nuclear Medicine and Molecular Imaging, 35(5) pp. 942-949.
Spahn, et al., "Wie soll die Hormontherapie beim kastrationsresistenten Prostatakarzinom fortgeführt werden?," 2012, Urologe, 51 pp. 15-19.
Sweat, et al., "Prostate-Specific Membrane Antigen Expression is Greatest in Prostate Adenocarcinoma and Lymph Node Metastases," 1998, Urology, 52(4) pp. 637-640.
Tang, et al., "Prostate targeting ligands based on N-acetylated α-linked acidic dipeptidase," 2003, Biochemical and Biophysical Research Communications, 307(1) pp. 8-14.
Tang, et al., "Updated Application of Prostate-Specific Membrane Antigen to the Diagnosis and Treatment of Prostate Cancer," 2008, National Journal of Andrology, 14(1) pp. 79-82.
Taylor, et al., "Prostate Cancer Targeting Motifs: Expression of anb3, Neurotensin Receptor 1,Prostate Specific Membrane Antigen, and Prostate Stem Cell Antigen in Human Prostate Cancer Cell Lines and Xenografts," 2012, The Prostate, 72(5) pp. 523-532.
Testa, et al., "Prostate Cancer: Sextant Localization with MR Imaging, MR Spectroscopy, and 11C-Choline PET/CT," 2007, Radiology, 244(3).
Thalmann, G., "Fortgeschrittenes Prostatakarzinom," 2012, Urologe, 51 pp. 7.
Tykvart, et al., "Rational design of urea-based glutamate carboxypeptidase II (GCPII) inhibitors as versatile tools for specific drug targeting and delivery," 2014, Bioorganic & Medicinal Chemistry, 22(15) pp. 4099-4108.
Uprimny, et al., "68Ga-PSMA ligand PET versus 18F-NaF PET: evaluation of response to 223Ra therapy in a prostate cancer patient," 2015, European Journal of Nuclear Medicine and Molecular Imaging, 42(2) pp. 362-363.
Vallabhajosula, et al., "Radioimmunotherapy of Prostate Cancer in Human Xenografts Using Monoclonal Antibodies Specific to Prostate Specific Membrane Antigen (PSMA): Studies in Nude Mice," 2004, The Prostate, 58(2) pp. 145-155.
Vavere, et al., "1-11C-Acetate as a PET Radiopharmaceutical for Imaging Fatty Acid Synthase Expression in Prostate Cancer," 2008, Journal of Nuclear Medicine, 49(2) pp. 327-334.
Wang, et al., "Bioisosterism of urea-based GCPII inhibitors: Synthesis and structure-activity relationship studies," 2010, Bioorganic & Medicinal Chemistry Letters, 20(1) pp. 392-397.
Wang, et al., "Development of Targeted Near-Infrared Imaging Agents for Prostate Cancer," 2014, Molecular Cancer Therapeutics, 13(11) pp. 2595-2606.
Weineisen, et al., "Synthesis and preclinical evaluation of DOTAGA-conjugated PSMA ligands for functional imaging and endoradiotherapy of prostate cancer," 2014, EJNMMI Research, 4(63).
Weissbach, L., "Welche Inhalte sollte eine living guideline besetzen?," 2012, Urologe, 51 pp. 57-59.
Whitaker, et al., "N-acetyl-L-aspartyl-L-glutamate peptidase-like 2 is overexpressed in cancer and promotes a pro-migratory and pro-metastatic phenotype," 2014, Oncogene, 33 pp. 5274-5287.
Wiehr, et al., "Pharmacokinetics and PET Imaging Properties of Two Recombinant Anti-PSMA Antibody Fragments in Comparison to their Parental Antibody," 2014, The Prostate, 74(7) pp. 743-755.
Wright, et al., "Expression of Prostate-Specific Membrane Antigen in Normal, Benign, and Malignant Prostate Tissues," 1995, Urologic Oncology, 1(1) pp. 18-28.
Wu, et al., "The molecular pruning of a phosphoramidate peptidomimetic inhibitor of prostate-specific membrane antigen," 2007, Bioorganic & Medicinal Chemistry, 15(23) pp. 7434-7443.
Yamaguchi, et al., "Prostate cancer: a comparative study of 11C-choline PET and MR imaging combined with proton MR spectroscopy," 2005, European Journal of Nuclear Medicine and Molecular Imaging, 32(7) pp. 742-748.
Zaheer, et al., "New Agents and Techniques for Imaging Prostate Cancer," 2009, Journal of Nuclear Medicine, 50(9) pp. 1387-1390.

(56) References Cited

OTHER PUBLICATIONS

Zechmann, et al., "Radiation dosimetry and first therapy results with a 124I/131 I-labeled small molecule (MIP-1095) targeting PSMA for prostate cancer therapy," 2014, European Journal of Nuclear Medicine and Molecular Imaging, 41 (7) pp. 1280-1292.
Zhang, et al., "A Remote Arene-Binding Site on Prostate Specific Membrane Antigen Revealed by Antibody-Recruiting Small Molecules," 2010, Journal of the American Chemical Society, 132(36) pp. 12711-12716.
Zhang, et al., "Prostate Specific Membrane Antigen (PSMA): A Novel Modulator of p38 for Proliferation, Migration, and Survival in Prostate Cancer Cells," 2013, The Prostate, 73(8) pp. 835-841.
Ahmadzadehfar, H. et al. "Early side effects and first results of radioligand therapy with (177)Lu-DKFZ-617 PSMA of castrate-resistant metastatic prostate cancer: a two-centre study." EJNMMI Res. Dec. 2015;5(1): 114. doi: 10.1186/s13550-015-0114-2. Epub Jun. 20, 2015.
Benesova, M. et al. "Preclinical Evaluation of a Tailor-Made DOTA-Conjugated PSMA Inhibitor with Optimized Linken Moiety for Imaging and Endoradiotherapy of Prostate Cancer." J Nucl Med. Jun. 2015;56(6):914-20. doi: 10.2967/jnumed.114.147413. Epub Apr. 16, 2015.
Benesova et al., "Linker Modification Strategies to Control the Prostate-Specific Membrane Antigen (PSMA)-Targeting and Pharmacokinetic Properties of DOTA-Conjugated PSMA Inhibitors," J Med Chem. 59(5):1761-75 (2016).
Khreish, F. et al.225Ac-PSMA-617/1 77Lu-PSMA-617 tandem therapy of metastatic castration-resistant prostate cancer: pilot experience. European Journal of Nuclear Medicine and Molecular Imaging (2020) 47:721-728. https://doi.org/10. 1007/s00259-019-04612-0.
Kratochwil, C et al. "Targeted alpha-Therapy of Metastatic Castration-Resistant Prostate Cancer with 225Ac-PSMA-617: Swimmer-Plot Analysis Suggests Efficacy Regarding Duration of Tumor Control"; J Nucl Med. 2018. vol. 59, No. 5, pp. 795-802, DOI: 10.2967/jnumed.117.203539, Jan. 11, 2018 (Jan. 11, 2018).
Kratochwil, et al. "225Ac-PSMA-617 for PSMA-Targeted a-Radiation Therapy of Metastatic Castration-Resistant Prostate Cancer." J Nucl Med 2016; 57:1941-1944. DOI: 10.2967/jnumed.116.178673.
Lymperis et al., "Radiometal-Dependent Biological Profile of the Radiolabeled Gastrin-Releasing Peptide Receptor Antagonist SB3 in Cancer Theranostics: Metabolic and Biodistribution Patterns Defined by Neprilysin," Bioconjug Chem. 29(5):1774-84 (2018).
Pratesi et al., "Design and solid phase synthesis of new DOTA conjugated {+}-biotin dimers planned to develop molecular weight-tuned avidin oligomers," Accepted Manuscript for Org Biomol Chem, pp. 1-15 (2013).
Chatalic, K. et al. Towards Personalized Treatment of Prostate Cancer: PSMA I&T, a Promising Prostate-Specific Membrane Antigen-Targeted Theranostic Agent. Theranostics. 2016; 6(6): pp. 849-861.
Rosar, F. et al. Molecular imaging and biochemical response assessment after a single cycle of [225Ac]Ac-PSMA-617/[177Lu]LuPSMA-617 tandem therapy in mCRPC patients whohave progressed on [177Lu]Lu-PSMA-617 monotherapy. Theranostics. 2021; 11(9): 4050-4060. doi: 10.7150/thno.56211.
Rossi et al., "N-Nmoc-L-glutamate, a new caged glutamate with high chemical stability and low pre-photolysis activity," J Biol Chem. 272(52):32933-9 (1997).
Hamilou, Z. et al. Treatment of Castration-naive Metastatic Prostate Cancer. Eur Urol Focus. Dec. 2017;3 (6):518-521. doi: 10.1016/j.euf.2018.02.004. Epub Feb. 27, 2018. PMID: 29500136.
Ikotun, O.F., et al. Investigation of a Vitamin B12 Conjugate as a PET Imaging Probe. 2014, ChemMedChem, 9: 1244-1251.
Kairemo K. et al., Lu-177-PSMA treatment for metastatic prostate cancer-case examples of miracle responses, Urology Herald, Mar. 7, 2018 , v. 6, No. 1, p. 65-75.
Majer, P. et al. Discovery of Orally Available Prodrugs of the Glutamate Carboxypeptidase II (GCPII) Inhibitor 2-Phosphonomethylpentanedioic Acid (2-PMPA). Journal of Medicinal Chemistry, 2016. 59 (6), pp. 2810-2819. DOI: 10.1021/acs.jmedchem.6b00062.
Emmett, L. et al. Lutetium 177 PSMA radionuclide therapy for men with prostate cancer: a review of the current literature and discussion of practical aspects of therapy. J Med Radiat Sci. Mar. 2017;64(1):52-60. doi: 10.1002/jmrs.227.
European Search Report in EP 20180928, completed Dec. 7, 2020.
International Search Report and Written Opinion for International Patent Application No. PCT/US2020/033584, mailed Aug. 14, 2020 (12 pages).
PCT International Search Report for PCT/US2008/073375, completed Oct. 26, 2008.
PCT International Search Report for PCT/US2009/061049, completed Mar. 15, 2010.
PCT International Search Report for PCT/US2009/061067, completed May 28, 2010.
PCT International Search Report for PCT/US2013/070007, completed Mar. 5, 2014.
PCT International Search Report for PCT/US2014/065467, dated Apr. 15, 2015.
Behr, S.C. et al. Phase I Study of CTT1057, an 18F-Labeled Imaging Agent with Phosphoramidate Core Targeting Prostate-Specific Membrane Antigen in Prostate Cancer. J Nucl Med 2019; 60:910-916.
Calais, J. et al. Prospective phase 2 trial of PSMA-targeted molecular Radiotherapy with 177Lu-PSMA-617 for metastatic castration-reSISTant Prostate Cancer (RESIST-PC): efficacy results of the UCLA cohort. J Nucl Med, 2021, 62:1440-1446.
Fani, M. et al. In vivo imaging of folate receptor positive tumor xenografts using novel 68Ga-NODAGA-folate conjugates. Mol Pharm. May 7, 2012;9(5):1136-45.
Jivan, S. et al. P 140: Fully automated preparation of [18F]CTT1057, a new prostate cancer imaging agent, prepared using the ORA Neptis Perform Synthesizer®. 22nd International Symposium on Radiopharmaceutical Sciences, Poster: S297, J Label Compd Radiopharm, 2017: 60 (Suppl. 1): S111-S640.
Rathke, H. et al. Repeated 177Lu-Labeled PSMA-617 Radioligand Therapy Using Treatment Activities of Up to 9.3 GBq. J Nucl Med, 2018, 59, 459-465.
Seifert, R. et al. Radioligand therapy using [177Lu]Lu-PSMA-617 in mCRPC: a pre-VISION single-center analysis. European Journal of Nuclear Medicine and Molecular Imaging (2020) 47:2106-2112.
Barraclough, H. et al. Biostatistics Primer: What a Clinician Ought to Know: Hazard Ratios. J. Thorac. Oneal. 2011, 978-982.
Bellmunt, J. et al. Castration-resistant prostate cancer: new science and therapeutic prospects. Therapeutic advances in medical oncology. May 2010; 2(3):189-207.
Drake, C.G. et al. Blocking the regulatory T cell molecule LAG-3 augments in vivo anti-tumor immunity in an autochthonous mode I of prostate cancer. Journal of Clinical Oncology, 2006 ASCO Annual Meeting Proceedings (Post-Meeting Edition). vol 24, No. 1SS (Jun. 20 Supplement), 2006: 2573.
Emmett, L. et al. ENZA-p: A randomized phase II trial using PSMA as a therapeutic agent and prognostic indicator in men with metastatic castration-resistant prostate cancer treated with enzalutamide. Poster. J. Clin. Oneal. 2021, 39, TPS177.
European Supplemental Search Report, prepared for EP Application No. 21757774, completed Jun. 5, 2024.
Fay, A.P. et al. Blocking the PD-1/PD-LI axis in advanced prostate cancer: are we moving in the right direction? Ann Transl Med 2019;7(Suppl I): S7.
Harsanyi et al. "Synthesis of 2-phosphinoxidomethyl- and 2-phosphonomethyl glutaric acid derivatives", Heteroatom Chemistry, vol. 16, No. 7, Jan. 1, 2005 (Jan. 1, 2005), pp. 562-565.
Koseki, Y. et al. Drug release is determined by the chain length of fatty acid-conjugated anticancer agent as one component of nanoprodrug. Bulletin of the Chemical Society of Japan. May 2016; 89(5): 540-5.
Nedelcovych, M.T. et al. JHU-2545 selectively shields salivary glands and kidneys during PSMA-targeted radiotherapy. bioRxiv. Oct. 30, 2018:457085.

(56) References Cited

OTHER PUBLICATIONS

Nedelcovych, M. et al. "Enhanced Brain Delivery of 2-(Phosphonomethyl)pentanedioic Acid Following Intranasal Administration of Its γ-Substituted Ester Prodrugs", Molecular Pharmaceutics, vol. 14, No. 10, Oct. 2, 2017 (Oct. 2, 2017), pp. 3248-3257.

Rich, J.N. Cancer stem cells in radiation resistance. Cancer research. Oct. 1, 2007; 67(19):8980-4.

Tan, G. et al. The efficacy and safety of abiraterone acetate in patients with high-risk prostate cancer: a meta-analysis based on six randomized control trials. Transl. Androl. Urol. 2020, 9, 1691-1699.

\* cited by examiner

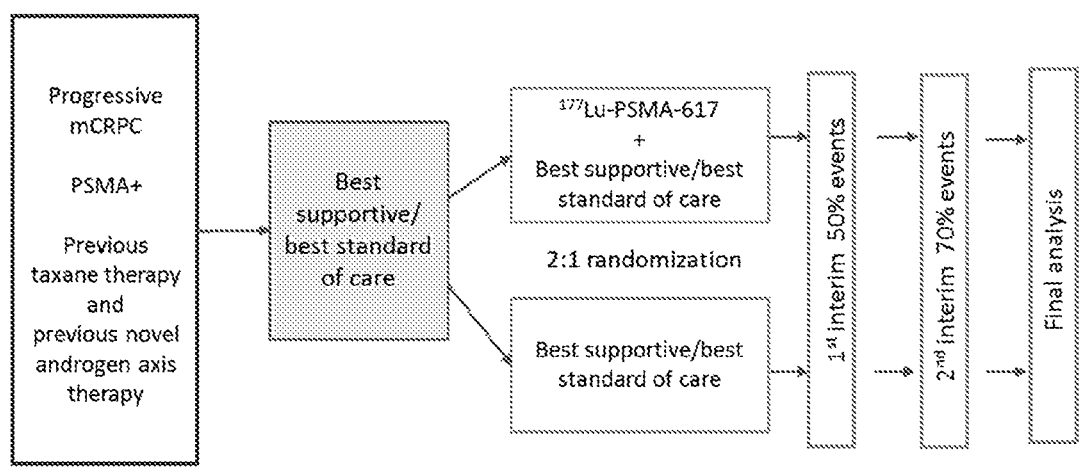

METHODS OF TREATING CANCER

CROSS-REFERENCE TO RELATED APPLICATIONS

This application is a national stage entry under 35 USC § 371 of PCT International Application Number PCT/US2019/027720, filed Apr. 16, 2019, which claims priority under 35 U.S.C. § 119 (e) to U.S. Provisional Application Ser. No. 62/659,016 filed on Apr. 17, 2018 and U.S. Provisional Application Ser. No. 62/670,442 filed on May 11, 2018, the entire disclosures of which are incorporated herein by reference.

FIELD OF THE INVENTION

The invention described herein pertains to drug delivery conjugates for targeted therapy. The invention described herein relates to methods of treating PSMA expressing cancers with a compound of the formula 1. The invention described herein also relates to methods of treating PSMA-expressing cancers with a compound of the formula 1 in patients where stable disease results after treatment with the compound of the formula 1.

BACKGROUND

Prostate specific membrane antigen (PSMA) is a type II cell surface membrane-bound glycoprotein with ~110 kD molecular weight, including an intracellular segment (amino acids 1-18), a transmembrane domain (amino acids 19-43), and an extensive extracellular domain (amino acids 44-750). While the functions of the intracellular segment and the transmembrane domains are currently believed to be insignificant, the extracellular domain is involved in several distinct activities. PSMA plays a role in the central nervous system, where it metabolizes N-acetyl-aspartyl glutamate (NAAG) into glutamic and N-acetyl aspartic acid. Accordingly, it is also sometimes referred to as an N-acetyl alpha linked acidic dipeptidase (NAALADase). PSMA is also sometimes referred to as a folate hydrolase I (FOLH I) or glutamate carboxypeptidase (GCP II) due to its role in the proximal small intestine where it removes γ-linked glutamate from poly-γ-glutamated folate and α-linked glutamate from peptides and small molecules.

PSMA is named largely due to its higher level of expression on prostate cancer cells; however, its particular function on prostate cancer cells remains unresolved. PSMA is over-expressed in the malignant prostate tissues when compared to other organs in the human body such as kidney, proximal small intestine, and salivary glands. Unlike many other membrane-bound proteins, PSMA undergoes rapid internalization into the cell in a similar fashion to cell surface bound receptors like vitamin receptors. PSMA is internalized through clathrin-coated pits and subsequently can either recycle to the cell surface or go to lysosomes. It has been suggested that the dimer and monomer form of PSMA are inter-convertible, though direct evidence of the interconversion is being debated. Even so, only the dimer of PSMA possesses enzymatic activity, and the monomer does not.

Though the activity of the PSMA on the cell surface of the prostate cells remains under investigation, it has been recognized by the inventors herein that PSMA represents a viable target for the selective and/or specific delivery of biologically active agents, including drug compounds to such prostate cells. One such drug compound is Compound 1

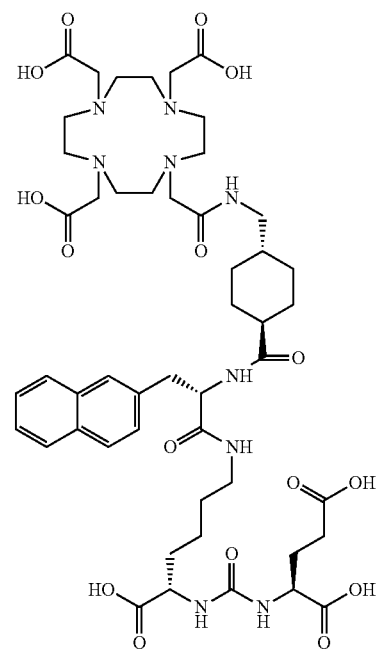

(a.k.a. (3S,10S,14S)-3-[(naphthalen-2-yl)methyl]-1,4,12-trioxo-1-[(1R,4S)-4-[[2-[4,7,10-tris(carboxymethyl)-1,4,7,10-tetraazacyclododecan-1-yl]acetamido]methyl]cyclohexyl]-2,5,11,13-tetraazahexadecane-10,14,16-tricarboxylic acid) wherein $^{177}$Lu is complexed to the compound, useful for the treatment of cancer as described in WO2015/055318. Compound 1 can be prepared according to the methods described in WO2015/055318, and WO2015/055318 is incorporated by reference for the preparation of Compound 1, as described in Example 3 and Example 5.

Without being bound by theory, it is believe that PSMA-617 consists of the pharmacophore ligand, glutamate-urea-lysine; the chelator DOTA (able to complex 177Lu); and a linker connecting these 2 entities. It is further believed that the urea-based binding motif allows the agent to bind to, and be internalized by PSMA at the site of disease. It is further believed that the binding of 177Lu-PSMA-617 leads to internalization through endocytosis and a sustained retention of the ligand and its bound radioactive cargo within the cancer cell.

Another such compound is the PSMA-imaging conjugate 4

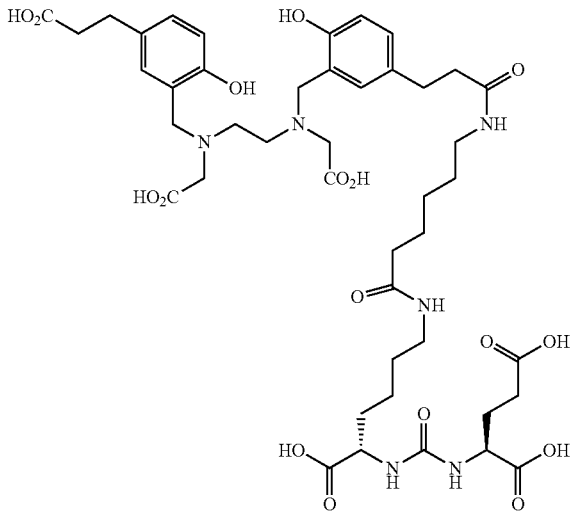

(a.k.a. 4,6,12,19-Tetraazadocosane-1,3,7-tricarboxylic acid, 22-[3-[[[2-[[[5-(2-carboxyethyl)-2-hydroxyphenyl]methyl] (carboxymethyl) amino]ethyl](carboxymethyeamino] methyl]-4-hydroxy-phenyl]-5,13,20-trioxo-,(3S,7S)) wherein $^{68}$Ga (or similar radioactive metal isotope) is complexed to the conjugate, useful for the imaging of cancer as described in Eder M, Schafer M, Bauder-Wust U, Hull W E, Wangler C, Mier W, et al. 68Ga-complex lipophilicity and the targeting property of a urea-based PSMA inhibitor for PET imaging. Bioconjug Chem. 2012; 23:688-97. PSMA imaging conjugate 4 can be prepared according to the methods described in (Eder, 2012), and (Eder, 2012) is incorporated by reference for the preparation of PSMA imaging conjugate 4, as described in the examples.

SUMMARY

In some embodiments, the present disclosure provides a method for treating a cancer in a patient in need of such treatment comprising, administering to the patient a therapeutically effective amount of Compound 1.

In some embodiments, the present disclosure provides use of Compound 1 for treating a cancer in a patient. In some aspects, the use comprises administering to the patient a therapeutically effective amount of the Compound 1.

In some embodiments, the present disclosure provides use of Compound 1 in the preparation of a medicament useful for the treatment of a cancer in a patient. In some aspects, the medicament comprises a therapeutically effective amount of Compound 1.

In some aspects of these embodiments, the cancer is a PSMA expressing cancer. In some aspects of these embodiments, the compound is at least about 98 percent pure. In some embodiments, the cancer is selected from the group consisting of a glioma, a carcinoma, a sarcoma, a lymphoma, a melanoma, a mesothelioma, a nasopharyngeal carcinoma, a leukemia, an adenocarcinoma, and a myeloma.

In some aspects of these embodiments, the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, metastatic breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, cancer of the urethra, cancer of the penis, prostate cancer, chronic leukemia, acute leukemia, lymphocytic lymphomas, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, glioma, brain stem glioma, pituitary adenoma, and adenocarcinoma of the gastroesophageal junction. In some aspects of these embodiments, the cancer is a primary or secondary brain cancer. In some aspects of these embodiments, the cancer is prostate cancer. In some aspects of these embodiments, the cancer is metastatic prostate cancer.

In some aspects of these embodiments, Compound 1 is administered in a parenteral dosage form. In some aspects of these embodiments, the parenteral dosage form is selected from the group consisting of intradermal, subcutaneous, intramuscular, intraperitoneal, intravenous, and intrathecal. In some aspects of these embodiments, the therapeutically effective amount is from about 2 GBq to about 13 GBq. In some aspects of these embodiments, the therapeutically effective amount is from about 4 GBq to about 11 GBq. In some aspects of these embodiments, the therapeutically effective amount is from about 5 GBq to about 10 GBq. In some aspects of these embodiments, the therapeutically effective amount is from about 6 GBq to about 9 GBq. In some aspects of these embodiments, the therapeutically effective amount is from about 6.5 GBq to about 8.5 GBq. In some aspects of these embodiments, the therapeutically effective amount is from about 7 GBq to about 8 GBq. In some aspects of these embodiments, the therapeutically effective amount is about 7.4 GBq. In some aspects of these embodiments, the total dose ranges from about 15 GBq to about 200 GBq. In some aspects of these embodiments, the total dose ranges from about 25 GBq to about 185 GBq. In some aspects of these embodiments, the total dose ranges from about 35 GBq to about 150 GBq. In some aspects of these embodiments, the total dose ranges from about 40 GBq to about 100 GBq. In some aspects of these embodiments, the total dose is about 44 GBq. In some aspects of these embodiments, the maximum duration of treatment of a subject is about 19 to 23 months.

In some aspects of these embodiments, the therapeutically effective amount is from 2 GBq to 13 GBq. In some aspects of these embodiments, the therapeutically effective amount is from 4 GBq to 11 GBq. In some aspects of these embodiments, the therapeutically effective amount is from 5 GBq to 10 GBq. In some aspects of these embodiments, the therapeutically effective amount is from 6 GBq to 9 GBq. In some aspects of these embodiments, the therapeutically effective amount is from 6.5 GBq to 8.5 GBq. In some aspects of these embodiments, the therapeutically effective amount is from 7 GBq to 8 GBq. In some aspects of these embodiments, the therapeutically effective amount is 7.4 GBq.

In some aspects of these embodiments, the therapeutically effective amount is from about 0.1 mg/m$^2$ to about 6.0 mg/m$^2$. In some aspects of these embodiments, the therapeutically effective amount is from about 0.1 mg/m$^2$ to about 5.0 mg/m². In some aspects of these embodiments, the therapeutically effective amount is from about 0.1 mg/m² to about 4.0 mg/m². In some aspects of these embodiments, the therapeutically effective amount is from about 0.1 mg/m² to about 3.5 mg/m². In some aspects of these embodiments, the therapeutically effective amount is from about 0.1 mg/m² to about 3.0 mg/m². In some aspects of these embodiments, the therapeutically effective amount is from about 0.1 mg/m² to about 2.5 mg/m². In some aspects of these embodiments, the therapeutically effective amount is from about 0.1 mg/m² to about 2.0 mg/m².

In some aspects of these embodiments, the therapeutically effective amount is from 0.1 mg/m² to 6.0 mg/m². In some aspects of these embodiments, the therapeutically effective amount is from 0.1 mg/m² to 5.0 mg/m². In some aspects of these embodiments, the therapeutically effective amount is from 0.1 mg/m² to 4.0 mg/m². In some aspects of these embodiments, the therapeutically effective amount is from 0.1 mg/m² to 3.5 mg/m². In some aspects of these embodiments, the therapeutically effective amount is from 0.1 mg/m² to 3.0 mg/m². In some aspects of these embodiments, the therapeutically effective amount is from 0.1 mg/m² to 2.5 mg/m². In some aspects of these embodiments, the therapeutically effective amount is from 0.1 mg/m² to 2.0 mg/m².

In other aspects, the methods and uses described herein further comprise imaging PSMA expression by the cancer. In some aspects of these embodiments, the step of imaging occurs before the step of administering. In some aspects of these embodiments, the imaging is performed by imaging wherein the imaging is selected from the group consisting of SPECT imaging, PET imaging, IHC, and FISH. In some aspects of these embodiments, the imaging is performed by SPECT imaging.

In some aspects of these embodiments, the step of imaging comprises administering to the patient a PSMA ligand-imaging conjugate of the formula 2

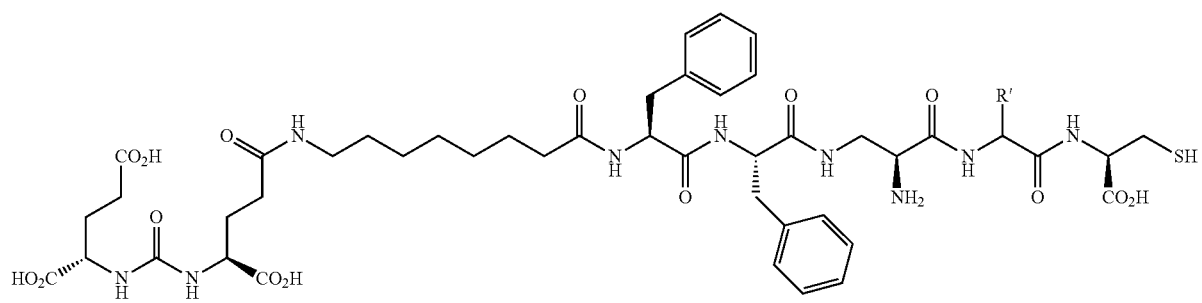

2 or a pharmaceutically acceptable salt thereof, wherein R' is hydrogen, or R' is selected from the group consisting of alkyl, aminoalkyl, carboxyalkyl, hydroxyalkyl, heteroalkyl, aryl, arylalkyl and heteroarylalkyl, each of which is optionally substituted, and wherein a radionuclide is bound to the conjugate.

In some aspects of these embodiments, the step of imaging comprises administering a PSMA ligand-imaging conjugate of the formula 3

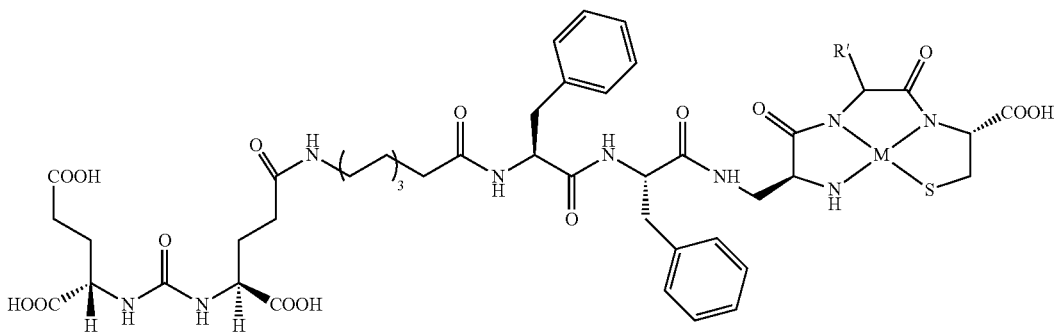

3 or a pharmaceutically acceptable salt thereof, wherein R' is hydrogen, or R' is selected from the group consisting of alkyl, aminoalkyl, carboxyalkyl, hydroxyalkyl, heteroalkyl, aryl, arylalkyl and heteroarylalkyl, each of which is optionally substituted, and wherein M is a cation of a radionuclide. In some aspects of these embodiments, M in the conjugate, or a pharmaceutically acceptable salt thereof, is selected from the group consisting of an isotope of gallium, an isotope of indium, an isotope of copper, an isotope of technetium, and an isotope of rhenium. In some aspects of these embodiments, M in the conjugate, or a pharmaceutically acceptable salt thereof, is an isotope of technetium.

In some aspects of these embodiments, the PSMA ligand-imaging conjugate is of the formula 2a

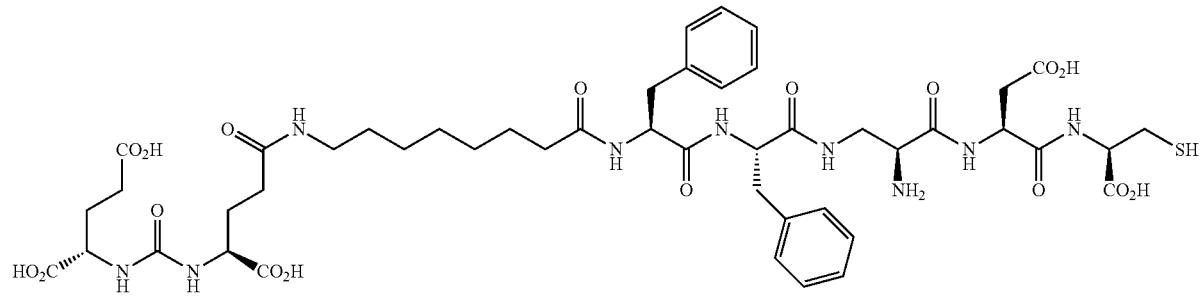

2a or a pharmaceutically acceptable salt thereof, wherein a radionuclide is bound to the conjugate. In some aspects of these embodiments, the PSMA ligand-imaging conjugate is of the formula 3a

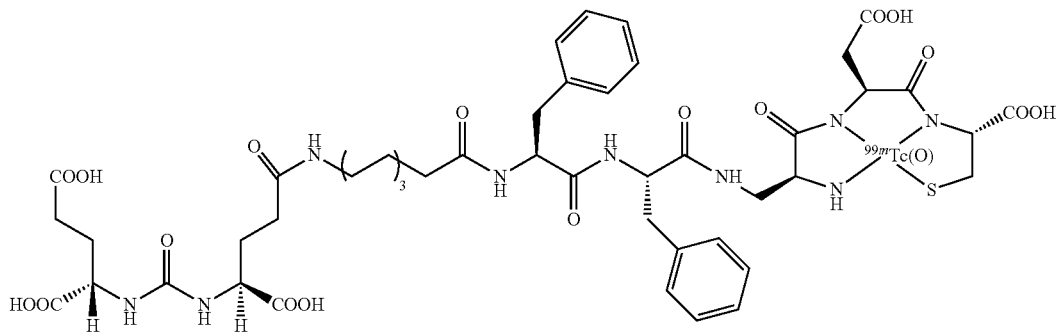

3a or a pharmaceutically acceptable salt thereof.

In some aspects of these embodiments, the step of imaging comprises administering to the patient a PSMA ligand-imaging conjugate of the formula 4

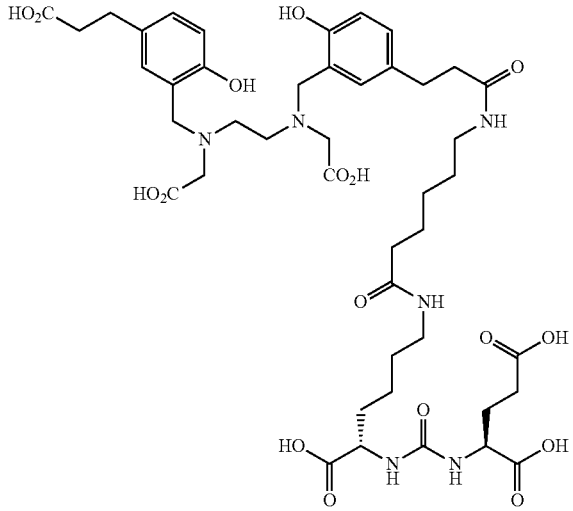 [SMILES: O=C(O)CCc1ccc(O)c(CN(CCN(CC(=O)O)Cc2cc(CCC(=O)NCCCCCC(=O)NCCCC[C@H](NC(=O)N[C@@H](CCC(=O)O)C(=O)O)C(=O)O)ccc2O)CC(=O)O)c1]

or a pharmaceutically acceptable salt thereof, wherein a radionuclide is bound to the conjugate. In some aspects of these embodiments, the radionuclide is $^{68}$Ga.

In other aspects, the methods and uses described herein further comprise determining the PSMA status of the patient by imaging. In some aspects of these embodiments, the imaging is SPECT imaging. In some aspects of these embodiments, the PSMA status of the patient correlates with a clinical benefit to the patient. In some aspects of these embodiments, the clinical benefit is selected from the group consisting of inhibition of tumor growth, stable disease, a partial response, and a complete response. In some aspects of these embodiments, the clinical benefit is stable disease. In some aspects of these embodiments, the PSMA positive lesions indicate functionally active PSMA.

In some aspects of these embodiments, the step of determining comprises administering to the patient a PSMA ligand-imaging conjugate of the formula 2

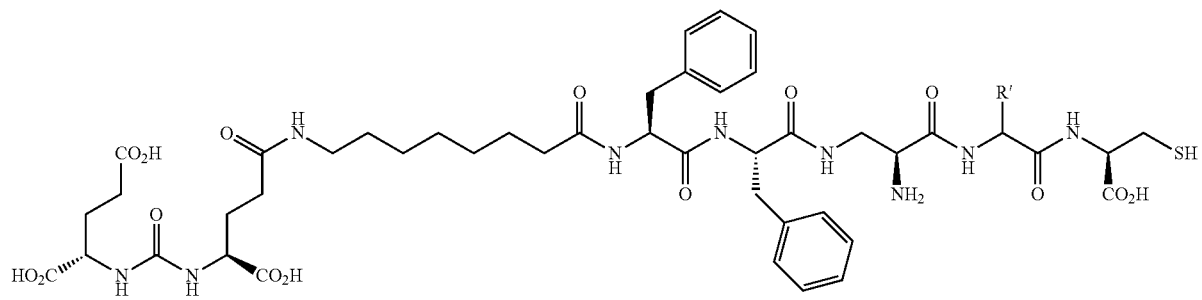

or a pharmaceutically acceptable salt thereof, wherein R' is hydrogen, or R' is selected from the group consisting of alkyl, aminoalkyl, carboxyalkyl, hydroxyalkyl, heteroalkyl, aryl, arylalkyl and heteroarylalkyl, each of which is optionally substituted, and wherein the conjugate is bound to a radionuclide.

In some aspects of these embodiments, the step of determining comprises administering a PSMA ligand-imaging conjugate of the formula 3

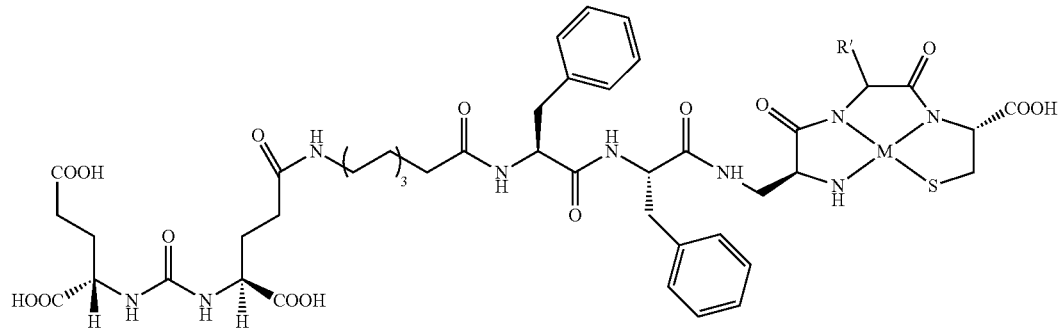

3 or a pharmaceutically acceptable salt thereof, wherein R' is hydrogen, or R' is selected from the group consisting of alkyl, aminoalkyl, carboxyalkyl, hydroxyalkyl, heteroalkyl, aryl, arylalkyl and heteroarylalkyl, each of which is optionally substituted, and wherein M is a cation of a radionuclide.

In some aspects of these embodiments, M in the conjugate, or a pharmaceutically acceptable salt thereof, is selected from the group consisting of an isotope of gallium, an isotope of indium, an isotope of copper, an isotope of technetium, and an isotope of rhenium. In some aspects of these embodiments, M in the conjugate, or a pharmaceutically acceptable salt thereof, is an isotope of technetium. In some aspects of these embodiments, the PSMA ligand-imaging conjugate is of the formula 2a

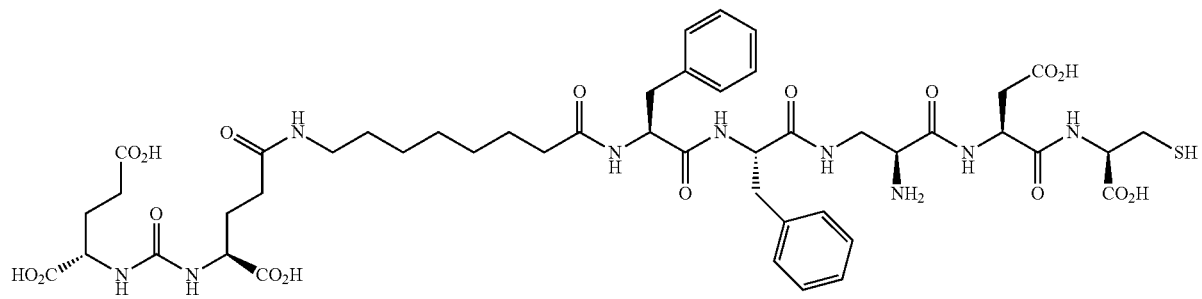

2a or a pharmaceutically acceptable salt thereof, wherein a radionuclide is bound to the conjugate.

In some aspects of these embodiments, the PSMA ligand-imaging conjugate is of the formula 3a

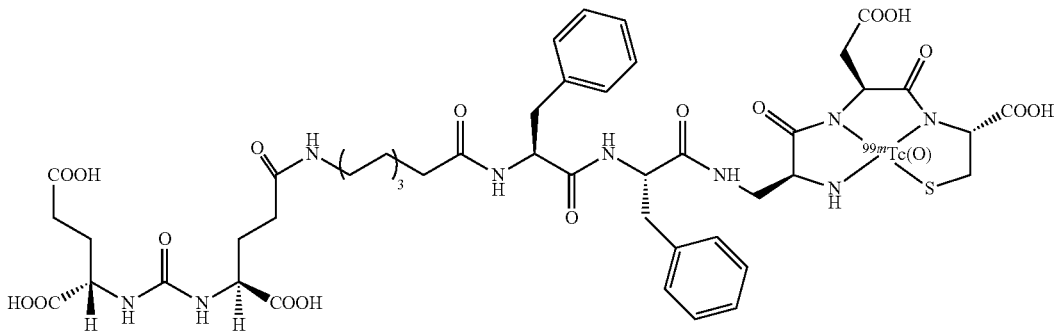

3a or a pharmaceutically acceptable salt thereof.

In some aspects of these embodiments, the step of determining comprises administering to the patient a PSMA ligand-imaging conjugate of the formula 4

4

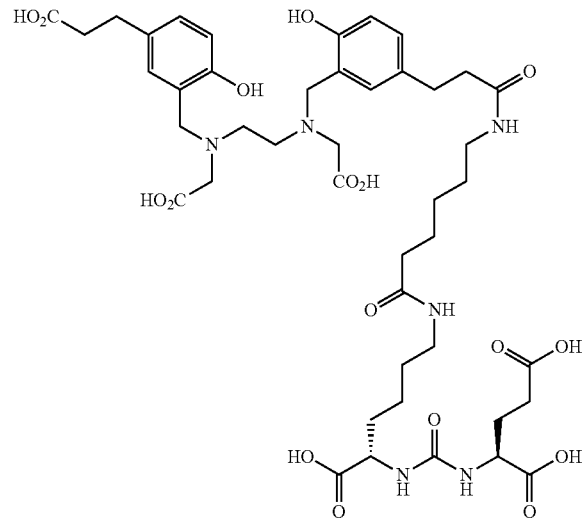

or a pharmaceutically acceptable salt thereof, wherein a radionuclide is bound to the conjugate. In some aspects of these embodiments, the radionuclide is $^{68}$Ga.

In other embodiments, the present disclosure provides a method of treating a cancer in a patient in need of such treatment comprising, administering to the patient a therapeutically effective amount of a Compound 1

1

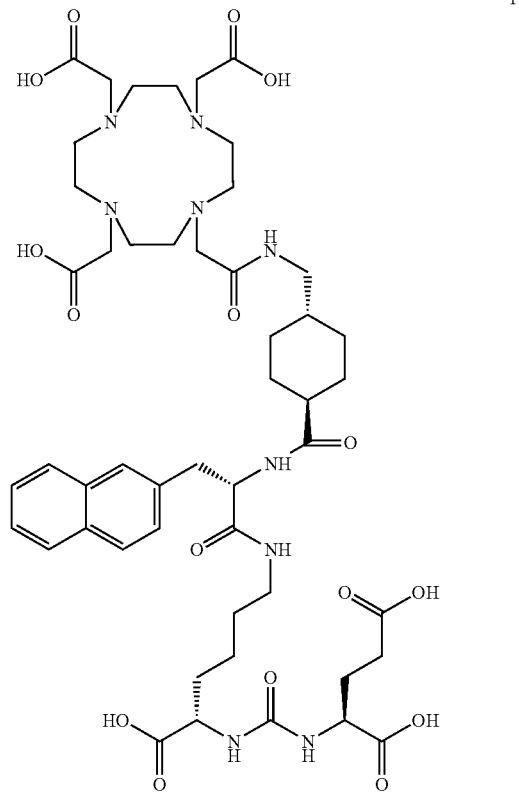 [SMILES: O=C(O)CC[C@H](NC(=O)N[C@@H](CCCCNC(=O)[C@H](Cc1ccc2ccccc2c1)NC(=O)[C@H]1CC[C@H](CNC(=O)CN2CCN(CC(=O)O)CCN(CC(=O)O)CCN(CC(=O)O)CC2)CC1)C(=O)O)C(=O)O]

wherein $^{177}$Lu is complexed to the Compound 1, wherein stable disease results after the Compound 1, or a pharmaceutically acceptable salt thereof, is administered.

In other embodiments, the present disclosure provides use of a Compound 1

1

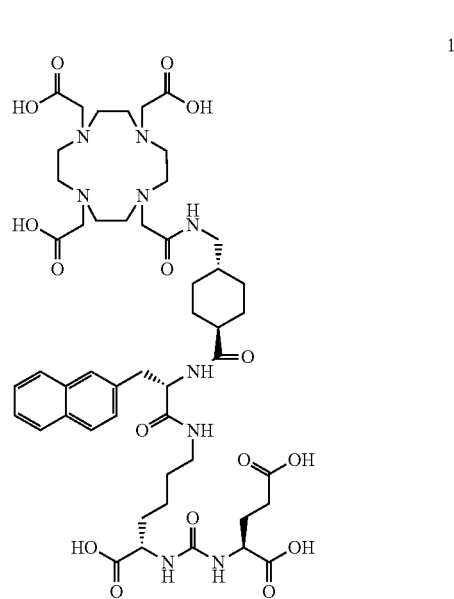 [SMILES: O=C(O)CC[C@H](NC(=O)N[C@@H](CCCCNC(=O)[C@H](Cc1ccc2ccccc2c1)NC(=O)[C@H]1CC[C@H](CNC(=O)CN2CCN(CC(=O)O)CCN(CC(=O)O)CCN(CC(=O)O)CC2)CC1)C(=O)O)C(=O)O]

wherein $^{177}$Lu is complexed to the Compound 1, wherein stable disease results after the Compound 1, or a pharmaceutically acceptable salt thereof, is administered. In some aspects of these embodiments, the use comprises administering to the patient a therapeutically effective amount of the Compound 1.

In other embodiments, the present disclosure provides use of a Compound 1

1

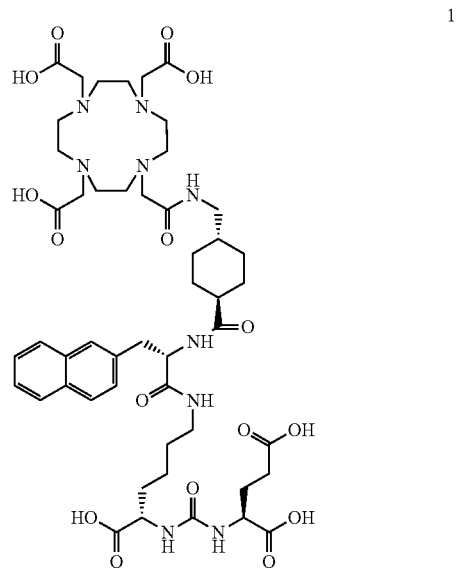 [SMILES: O=C(O)CC[C@H](NC(=O)N[C@@H](CCCCNC(=O)[C@H](Cc1ccc2ccccc2c1)NC(=O)[C@H]1CC[C@H](CNC(=O)CN2CCN(CC(=O)O)CCN(CC(=O)O)CCN(CC(=O)O)CC2)CC1)C(=O)O)C(=O)O]

wherein $^{177}$Lu is complexed to the Compound 1, in the preparation of a medicament useful for the treatment of a cancer in a patient, wherein stable disease results after the Compound 1, or a pharmaceutically acceptable salt thereof, is administered. In some aspects, the medicament comprises a therapeutically effective amount of the Compound 1, or a pharmaceutically acceptable salt thereof.

In some aspects of these embodiments, the patient has been treated with at least one prior treatment. In some aspects of these embodiments, the at least one prior treatment is selected from the group consisting of an androgen axis systemic treatment, a chemotherapeutic agent, surgery, radiation therapy, immunotherapy, photodynamic therapy, stem cell therapy, and hyperthermia. In some aspects of these embodiments, the at least one prior treatment is a systemic treatment. In some aspects of these embodiments, the systemic treatment is selected from the group consisting of palifosfamide, 5-fluorouracil, capecitabine, pemetrexed, cisplatin, carboplatin, gemcitabine, paclitaxel, vinorelbine, eribulin, docetaxel, cyclophosphamide, doxorubicin, regorafinib, and combinations thereof. In some aspects of these embodiments, the cancer is a PSMA expressing cancer. In some aspects of these embodiments, the compound is at least about 98 percent pure.

Embodiments of the invention are further described by the following enumerated clauses:

1. A method for treating a cancer in a patient in need of such treatment comprising, administering to the patient a therapeutically effective amount of a compound of the formula 1 ort

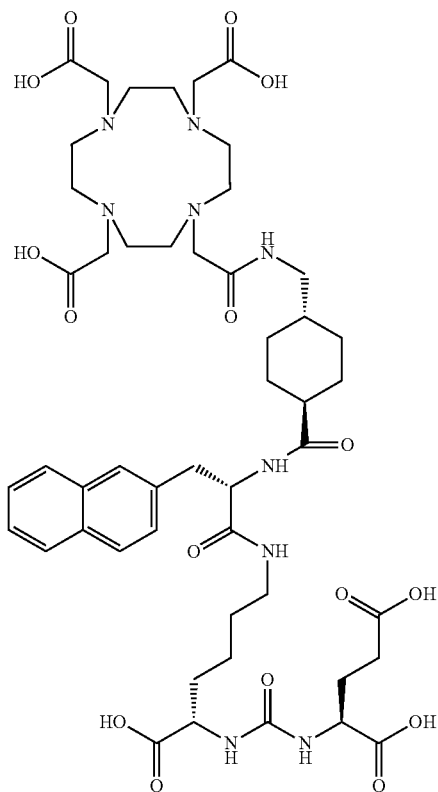

wherein the compound is complexed with a metal.

2. The method of clause 1, wherein the cancer is a PSMA expressing cancer.

3. The method of clause 1 or 2, wherein the compound of the formula 1 is at least about 98 percent pure.

4. The method of any one of the preceding clauses, wherein the cancer is prostate cancer.

5. The method of any one of the preceding clauses, wherein the cancer is metastatic castration-resistant prostate cancer.

6. The method of any one of the preceding clauses, wherein the compound of the formula 1, is administered in a parenteral dosage form.

7. The method of clause 6, wherein the parenteral dosage form is selected from the group consisting of intradermal, subcutaneous, intramuscular, intraperitoneal, intravenous, and intrathecal.

8. The method of any one of the preceding clauses, wherein the therapeutically effective amount is from about 2 GBq to about 13 GBq.

9. The method of any one of the preceding clauses, wherein the therapeutically effective amount is from about 4 GBq to about 11 GBq.

10. The method of any one of the preceding clauses, wherein the therapeutically effective amount is from about 5 GBq to about 10 GBq.

11. The method of any one of the preceding clauses, wherein the therapeutically effective amount is from about 6 GBq to about 9 GBq.

12. The method of any one of the preceding clauses, wherein the therapeutically effective amount is from about 6.5 GBq to about 8.5 GBq.

13. The method of any one of the preceding clauses, wherein the therapeutically effective amount is from about 7 GBq to about 8 GBq.

14. The method of any one of the preceding clauses, wherein the therapeutically effective amount is about 7.4 GBq.

15. The method of any one of the preceding clauses, further comprising imaging PSMA expression by the cancer.

16. The method of clause 15, wherein the imaging occurs before the step of administering.

17. The method of clause 16, wherein the imaging is performed by imaging and wherein the imaging is selected from the group consisting of SPECT imaging, PET imaging, IHC, and FISH.

18. The method of clause 17, wherein the imaging is performed by SPECT imaging.

19. The method of any one of clauses 1 to 14, further comprising determining the PSMA status of the patient by imaging.

20. The method of clause 19, wherein the imaging is SPECT imaging.

21. The method of clause 20, wherein the PSMA status of the patient correlates with a clinical benefit to the patient.

22. The method of clause 21, wherein the clinical benefit is selected from the group consisting of inhibition of tumor growth, stable disease, a partial response, and a complete response.

23. The method of clause 22, wherein the clinical benefit is stable disease.

24. The method of clause 21, wherein at least one PSMA positive lesion indicates functionally active PSMA.

25. The method of any one of the preceding clauses, wherein the patient has been treated with at least one prior treatment.

26. The method of clause 25, wherein the at least one prior treatment is selected from the group consisting of an androgen axis systemic treatment, chemotherapeutic agent, surgery, radiation therapy, immunotherapy, photodynamic therapy, stem cell therapy, and hyperthermia.

27. The method of clause 26, wherein the at least one prior treatment is an androgen axis drug systemic treatment.

28. The method of clause 26, wherein the at least one prior treatment is selected from the group consisting of abiraterone, orteronel, galeterone, seviteronel, apalutamide, enzalutamide, and combinations thereof.

29. The method of clause 25, wherein the at least one prior treatment is selected from the group consisting of palifosfamide, 5-fluorouracil, capecitabine, pemetrexed, cisplatin, carboplatin, gemcitabine, paclitaxel, vinorelbine, eribulin, docetaxel, cyclophosphamide, doxorubicin, regorafinib, and combinations thereof.

30. The method of any one of the preceding clauses, wherein the compound of the formula 1 is administered in combination with a second treatment.

31. The method of clause 30, wherein the second treatment is best supportive treatment.

32. The method of clause 30, wherein the second treatment is best standard of care treatment.

33. The method of clause 30, wherein the second treatment is best supportive/best standard of care treatment.

34. The method of clause 30, wherein the second treatment is an androgen axis systemic treatment.

35. The method of clause 34, wherein the androgen axis systemic treatment is selected from the group consisting of abiraterone, orteronel, galeterone, seviteronel, apalutamide, enzalutamide, and combinations thereof.

36. The method of clause 30, wherein the second treatment is radiation therapy.

37. The method of clause 30, wherein the radiation therapy is external beam radiation therapy (EBRT).

38. The method of any one of the preceding clauses, wherein the compound of the formula 1 is administered on a schedule of once per week.

39. The method of any one of the clauses 1 to 37, wherein the compound of the formula 1 is administered on a schedule of once per every 2 weeks.

40. The method of any one of the clauses 1 to 37, wherein the compound of the formula 1 is administered on a schedule of once per every 3 weeks.

41. The method of any one of the clauses 1 to 37, wherein the compound of the formula 1 is administered on a schedule of once per every 4 weeks.

42. The method of any one of the clauses 1 to 37, wherein the compound of the formula 1 is administered on a schedule of once per every 5 weeks.

43. The method of any one of the clauses 1 to 37, wherein the compound of the formula 1 is administered on a schedule of once per every 6 weeks.

44. The method of any one of the clauses 1 to 37, wherein the compound of the formula 1 is administered on a schedule of once per every 7 weeks.

45. The method of any one of the clauses 1 to 37, wherein the compound of the formula 1 is administered on a schedule of once per every 8 weeks.

46. The method of any one of the clauses 1 to 37, wherein the compound of the formula 1 is administered on a schedule of once per every 4 to 6 weeks.

47. The method of any one of clauses 38 to 46, wherein the compound of the formula 1 is administered for about 2 to 8 cycles of the schedule.

48. The method of any one of clauses 38 to 46, wherein the compound of the formula 1 is administered for about 3 to 7 cycles of the schedule.

49. The method of any one of clauses 38 to 46, wherein the compound of the formula 1 is administered for about 4 to 6 cycles of the schedule.

50. The method of any one of the preceding clauses, wherein the metal complexed to the Compound 1 or the Compound 2 is selected from the group consisting of $^{90}$Y, $^{177}$Lu, $^{64}$Cd, $^{153}$Gd, $^{155}$Gd, $^{157}$Gd, $^{213}$Bi, and $^{225}$Ac.

51. The method of clause 50, wherein the metal complexed to the Compound 1 is $^{177}$Lu.

52. The method of clause 50, wherein the metal complexed to the Compound 1 is $^{225}$Ac.

BRIEF DESCRIPTION OF THE DRAWINGS

FIG. 1 shows a schematic of the treatment method design.

DEFINITIONS

In accordance with the invention, "functionally active PSMA" means a cell surface membrane-bound glycoprotein that binds to a PSMA ligand. It will be appreciated that PSMA ligands are well known to those skilled in the art such as those described in US patent publication no. US 2010/0324008 A1, incorporated herein by reference.

In accordance with the invention, "clinical benefit" means a response of a patient to treatment with Compound 1 where the response includes overall survival of the patient, ability to receive four or more cycles of therapy (e.g., four weeks of therapy) with Compound 1, inhibition of tumor growth, stable disease, a partial response, and/or a complete response, among other clinical benefits defined by the Food and Drug Administration in the United States of America.

In accordance with the invention, "inhibition of tumor growth" means reduction in tumor size, complete disappearance of a tumor, or growth of a patient tumor of less than 30% over the course of therapy with Compound 1.

In accordance with the invention, "stable disease" means no material progression of disease in a patient over the course of therapy with Compound 1.

In accordance with the invention, "a partial response" means a decrease in tumor size of 30% or greater in a patient treated with Compound 1.

In accordance with the invention, "a complete response" means the disappearance of detectable disease in a patient treated with Compound 1.

In accordance with the invention, "prior treatment" means the patient has been treated with at least one prior treatment known in the art. It will be appreciated that a prior treatment can be any treatment known to those of skill in the art, including, but not limited, chemotherapeutic agent, surgery, radiation therapy, immunotherapy, photodynamic therapy, stem cell therapy, hyperthermia, and the like. Prior treatments can include systemic treatments including, but not limited to treatment with abiraterone, orteronel, galeterone, seviteronel, apalutamide, enzalutamide, palifosfamide, 5-fluorouracil, capecitabine, pemetrexed, cisplatin, carboplatin, gemcitabine, paclitaxel, vinorelbine, eribulin, docetaxel, cyclophosphamide, doxorubicin, regorafinib, and combinations thereof.

In accordance with the inventions, the term "alkyl" includes a chain of carbon atoms, which is optionally branched. It will be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. Illustratively, such particularly limited length alkyl groups, including $C_1$-$C_8$, $C_1$-$C_6$, and $C_1$-$C_4$ may be referred to as lower alkyl. It is appreciated herein that shorter alkyl, alkenyl, and/or alkynyl groups may add less lipophilicity to the compound and accordingly will have different pharmacokinetic behavior. In embodiments of the invention described herein, it is to be understood, in each case, that the recitation of alkyl refers to alkyl as defined herein, and optionally lower alkyl. Illustrative alkyl groups include, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. As used herein, a "carboxyalkyl" group includes a combination of an "alkyl" group as described herein with a "carboxy" group. As used herein, a "hydroxyalkyl" group includes a combination of an "alkyl" group as described herein with a "hydroxy" group. As used herein, a "aminoalkyl" group includes a combination of an "alkyl" group as described herein with a "amino" group.

In accordance with the invention, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium.

In accordance with the invention, the term "aryl" includes monocyclic and polycyclic aromatic carbocyclic groups having from 6 to 14 ring carbon atoms, each of which may be optionally substituted. Illustrative aromatic carbocyclic groups described herein include, but are not limited to, phenyl, naphthyl, and the like. In accordance with the invention, the term "heteroaryl" includes aromatic heterocyclic groups, having from 5 to 10 ring atoms, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like. In accordance with the invention, the term "heteroarylalkyl" includes a combination of an "alkyl" group as described herein with a "heteroaryl" group described herein. In accordance with the invention, the term "arylalkyl" includes a combination of an "alkyl" group as described herein with a "aryl" group described herein, for example a benzyl group.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

In accordance with the invention, the term "administering" as used herein includes all means of introducing the Compound 1 and PSMA ligand-imaging conjugates described herein to the patient, including, but not limited to, oral (po), intravenous (iv), intramuscular (im), subcutaneous (sc), transdermal, inhalation, buccal, ocular, sublingual, vaginal, rectal, and the like. The Compound 1 and PSMA ligand-imaging conjugates described herein may be administered in unit dosage forms and/or formulations containing conventional nontoxic pharmaceutically-acceptable carriers, adjuvants, and vehicles.

In accordance with the invention, "becquerel" means a SI derived unit of radioactivity as it is commonly understood by one of skill in the art. One becquerel is defined as the activity of a quantity of radioactive material in which one nucleus decays per second. A becquerel is therefore equivalent to an inverse second, s−1. The becquerel is known to one of skill in the art as the successor of the curie (Ci), an older, non-SI unit of radioactivity based on the activity of 1 gram of radium-226. The curie is defined as 3.7. 1010 s−1, or 37 GBq.

In accordance with the invention, "curie" or "Ci" means a unit of radioactivity named after the French physicist and chemist Marie Curie as commonly understood by one of skill in the art. The prefixes milli and micro are from the metric system and represent 0.001 and 0.000001, respectively. So, a millicurie (mCi) is 0.001 curie. A microcurie (μCi) is 0.000001 curie.

DETAILED DESCRIPTION

In accordance with Applicant's invention described herein, the embodiments of the numbered clauses provided in the summary above, or any combination thereof, are contemplated for combination with any of the embodiments described in the Detailed Description section of this patent application.

Referring to FIG. 1, the method design can be described according to the schematic shown. In some embodiments, stratification factors for the design include, but are not limited to serum lactate dehydrogenase (LDH) (</=260 IU/L v. >260 IU/L), presence of liver metastases, ECOG score (0-1 v. 2), inclusion of NAAD in best supportive/best standard of care, and the like. In some embodiments, the primary endpoint can be overall survival. In some embodiments, secondary endpoints include, but are not limited to, radiographic progression-free survival (rPFS), RECIST response, time to first symptomatic skeletal event (SSE), and the like. In some embodiments, additional secondary endpoints include, but are not limited to, safety and tolerability, heather-related quality of life (HRQoL; EQ-5D-5L, FACT-P and Brief Pain Inventory—Short FORM [BPI-SF]), health economics, progression-free survival (PFS) (radiological, clinical or PSA progression), biochemical response, such as PSA levels, alkaline phosphatase level, and/or lactate dehydrogenase level. In some embodiments, an endpoint for the treatment methods described herein can be a patient who has achieved a >/=50% decrease from baseline that is confirmed by a second PSA measurement >/=4 weeks. In some embodiments, an endpoint for the treatment methods described herein can be a patient who has achieved a >/=40% decrease from baseline that is confirmed by a second PSA measurement >/=4 weeks. In some embodiments, an endpoint for the treatment methods described herein can be a patient who has achieved a >/=30% decrease from baseline that is confirmed by a second PSA measurement >/=4 weeks.

In one embodiment, the methods described herein can be used for both human clinical medicine and veterinary applications. Thus, a "patient" can be administered the Compound 1 or PSMA ligand-imaging conjugates described herein, and can be human or, in the case of veterinary applications, can be a laboratory, agricultural, domestic, or wild animal. In one aspect, the patient can be a human, a laboratory animal such as a rodent (e.g., mice, rats, hamsters, etc.), a rabbit, a monkey, a chimpanzee, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

In some embodiments, patients with PSMA positive scans can be randomized in a 2:1 ratio to receive either Compound 1 plus best supportive/best standard of care or to receive best supportive/best standard of care only. In some embodiments, best supportive/best standard of care can be determined by the treating physician/investigator. In some embodiments, best supportive/best standard of care can be determined by the treating physician/investigator, but will exclude investigational agents, cytotoxic chemotherapy, other systemic radioisotopes, and hemi-body radiotherapy. In some embodiments, novel androgen axis drugs [NAADs], such as abiraterone or enzalutamide, are allowed.

In some embodiments, patients will be monitored throughout the 6 to 10-month treatment period for survival, disease progression, and adverse events. In some embodiments, a long-term follow-up period can include the collection of survival and treatment updates, adverse events assessment, as well as blood for hematology and chemistry testing.

In some embodiments, the patient is 18 Years of age or older. In some embodiments, the patient is a male. In some embodiments, the patient has previously been diagnosed with prostate cancer. In some embodiments, the patient has been previously diagnosed with metastatic castration-resistant prostate cancer (mCRPC). In some embodiments, the patient meets one or more criteria, selected from the group consisting of Eastern Cooperative Oncology Group (ECOG) performance status of 0 to 2; a life expectancy at least 6 months; histological, pathological, and/or cytological confirmation of prostate cancer; a positive $^{68}$Ga-PSMA-11 PET/CT scan; prior orchiectomy and/or ongoing androgen deprivation therapy and a castrate level of serum testosterone (<50 ng/dL or <1.7 nmol/L); previously received at least one NAAD, such as enzalutamide and/or abiraterone; previously treated with at least 1 or 2 previous taxane regimens, wherein a taxane regimen comprises a minimum exposure of 2 cycles of a taxane, or previously received only one taxane regimen, and a. the patient is not willing to receive a second taxane regimen, or b. The patient's physician deems him unsuitable to receive a second taxane regimen, such as due to frailty assessed by geriatric or health status evaluation or intolerance; progressive mCRPC, such as documented progressive mCRPC based on at least one criteria, such as a. serum PSA progression defined as 2 consecutive increases in PSA over a previous reference value measured at least 1 week prior, where the minimal start value is 2.0 ng/mL, b. soft-tissue progression defined as an increase ≥20% in the sum of the diameter (SOD) (short axis for nodal lesions and long axis for non-nodal lesions) of all target lesions based on the smallest SOD since treatment started or the appearance of one or more new lesions, and c. progression of bone disease, such as evaluable disease or new bone lesions(s) by bone scan (2+2 PCWG3 criteria); at least one metastatic lesion that is present on baseline CT, MRI, or bone scan imaging obtained ≤28 days prior to beginning therapy with Compound 1; recovered to ≤Grade 2 from all clinically significant toxicities related to prior therapies, such as prior chemotherapy, radiation, immunotherapy, and the like; adequate organ function, such as a. bone marrow reserve including white blood cell (WBC) count ≥2.5×109/L (2.5× 10^9/L is equivalent to 2.5×10$^3$/µL and 2.5×K/µL and 2.5× 10$^3$/cumm and 2500/µL) or absolute neutrophil count (ANC) ≥1.5×10$^9$/L (1.5×10$^9$/L is equivalent to 1.5×10$^3$/µL and 1.5×K/µL and 1.5×10$^3$/cumm and 1500/µL), platelets≥100× 10^9/L (100×10^9/L is equivalent to 100×10^3/µL and 100× K/µL and 100×10^3/cumm and 100,000/µL), and/or hemoglobin≥9 g/dL (9 g/dL is equivalent to 90 g/L and 5.59 mmol/L); b. hepatic, such as total bilirubin ≤1.5×the institutional upper limit of normal (ULN) (for patients with known Gilbert's Syndrome ≤3×ULN is permitted), alanine aminotransferase (ALT) or aspartate aminotransferase (AST)≤3.0×ULN OR ≤5.0×ULN for patients with liver metastases, and c. renal, such as serum creatinine ≤1.5×ULN or creatinine clearance ≥50 mL/min; albumin >3.0 g/dL (3.0 g/dL is equivalent to 30 g/L); and a stable bisphosphonate or denosumab regimen for ≥30 days prior to treatment.

In some embodiments, a patient may not receive treatment if the patient has one of more of previous treatment with Strontium-89, Samarium-153, Rhenium-186, Rhenium-188, Radium-223 or hemi-body irradiation within about 6 months prior treatment; previous PSMA-targeted radioligand therapy; previous systemic anti-cancer therapy (e.g. chemotherapy, immunotherapy or biological therapy [including monoclonal antibodies]) within about 28 days prior to treatment; previous administration of investigational agents within about 28 days prior to treatment; a known hypersensitivity to the components of the therapy or its analogs; any other concurrent cytotoxic chemotherapy, immunotherapy, radioligand therapy, or investigational therapy; a transfusion within about 30 days of treatment; a history of CNS metastases that have received therapy (surgery, radiotherapy, gamma knife) and are neurologically stable, asymptomatic, and not receiving corticosteroids for the purposes of maintaining neurologic integrity; a superscan as seen in the baseline bone scan; a symptomatic cord compression, or clinical or radiologic findings indicative of impending cord compression; concurrent serious (as determined by a physician) medical conditions, including, but not limited to, New York Heart Association class III or IV congestive heart failure, history of congenital prolonged QT syndrome, uncontrolled infection, active hepatitis B or C, or other significant co-morbid conditions that in the opinion of the investigator would impair treatment or cooperation; or been diagnosed with other malignancies that are expected to alter life expectancy or may interfere with disease assessment.

In various embodiments, the cancers described herein can be a cancer cell population that is tumorigenic, including benign tumors and malignant tumors, or the cancer can be non-tumorigenic. The cancer can arise spontaneously or by such processes as mutations present in the germline of the patient or somatic mutations, or the cancer can be chemically-, virally-, or radiation-induced. Cancers applicable to the invention described herein include, but are not limited to, a glioma, a carcinoma, a sarcoma, a lymphoma, a melanoma, a mesothelioma, a nasopharyngeal carcinoma, a leukemia, an adenocarcinoma, and a myeloma.

In some aspects the cancers can be lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, metastatic breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, cancer of the urethra, cancer of the penis, prostate cancer, chronic leukemia, acute leukemia, lymphocytic lymphomas, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, glioma, brain stem glioma, pituitary adenoma, and adenocarcinoma of the gastroesophageal junction.

Compound 1 has the formula

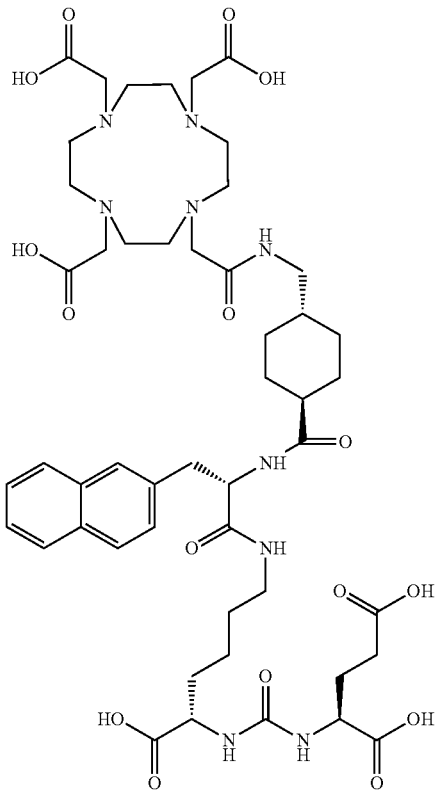

1 wherein $^{177}$Lu is complexed to the compound.

In other embodiments, any of a variety of PSMA ligand-imaging conjugates detectable by PET imaging, SPECT imaging, and the like can be used. The exact manner of imaging is not limited to the imaging agents described herein. Collectively, the PSMA ligand-imaging conjugates useful for imaging described herein, including those described by formulas and the agents useful for PET imaging, SPECT imaging, etc. are referred to as "PSMA ligand-imaging conjugates."

In one embodiment, the Compound 1 and PSMA ligand-imaging conjugates described herein bind to expressed PSMA on cancer cells. In one illustrative aspect, the Compound 1 and PSMA ligand-imaging conjugates are capable of differentially binding to PSMA on cancer cells compared to normal cells due to preferential expression (or overexpression) of PSMA on the cancer cells.

In other embodiments of the methods described herein, pharmaceutically acceptable salts of the Compound 1 and PSMA ligand-imaging conjugates described herein are provided. Pharmaceutically acceptable salts of the Compound 1 and PSMA ligand-imaging conjugates described herein include acid addition and base salts thereof.

Suitable acid addition salts are formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts of the Compound 1 and PSMA ligand-imaging conjugates described herein are formed from bases which form non-toxic salts. Illustrative examples include the arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

In one embodiment, the Compound 1 and PSMA ligand-imaging conjugates described herein may be administered as a formulation in association with one or more pharmaceutically acceptable carriers. The carriers can be excipients. The choice of carrier will to a large extent depend on factors such as the particular mode of administration, the effect of the carrier on solubility and stability, and the nature of the dosage form. Pharmaceutical compositions suitable for the delivery of Compound 1 and PSMA ligand-imaging conjugates described herein and methods for their preparation will be readily apparent to those skilled in the art. Such compositions and methods for their preparation may be found, for example, in Remington: The Science & Practice of Pharmacy, 21th Edition (Lippincott Williams & Wilkins, 2005), incorporated herein by reference.

In one illustrative aspect, a pharmaceutically acceptable carrier includes any and all solvents, dispersion media, coatings, antibacterial and antifungal agents, isotonic and absorption delaying agents, and the like, and combinations thereof, that are physiologically compatible. In some embodiments, the carrier is suitable for parenteral administration. Pharmaceutically acceptable carriers include sterile aqueous solutions or dispersions and sterile powders for the extemporaneous preparation of sterile injectable solutions or dispersions. Supplementary active compounds can also be incorporated into compositions of the invention.

In various embodiments, liquid formulations may include suspensions and solutions. Such formulations may comprise a carrier, for example, water, ethanol, polyethylene glycol, propylene glycol, methylcellulose or a suitable oil, and one or more emulsifying agents and/or suspending agents. Liquid formulations may also be prepared by the reconstitution of a solid.

In one embodiment, an aqueous suspension may contain the active materials in admixture with appropriate excipients. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally-occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and a hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, ascorbic acid, ethyl, n-propyl, or p-hydroxybenzoate; or one or more coloring agents.

In one illustrative embodiment, dispersible powders and granules suitable for preparation of an aqueous suspension by the addition of water provide the active ingredient in admixture with a dispersing or wetting agent, suspending agent and one or more preservatives. Additional excipients, for example, coloring agents, may also be present.

Suitable emulsifying agents may be naturally-occurring gums, for example, gum acacia or gum tragacanth; naturally-occurring phosphatides, for example, soybean lecithin; and esters including partial esters derived from fatty acids and hexitol anhydrides, for example, sorbitan mono-oleate, and condensation products of the said partial esters with ethylene oxide, for example, polyoxyethylene sorbitan monooleate.

In other embodiments, isotonic agents, for example, sugars, polyalcohols such as mannitol, sorbitol, or sodium chloride can be included in the composition. Prolonged absorption of injectable compositions can be brought about by including in the composition an agent which delays absorption, for example, monostearate salts and gelatin.

Illustrative formats for oral administration include tablets, capsules, elixirs, syrups, and the like.

Depending upon the cancer type as described herein, the route of administration and/or whether the Compound 1 and/or PSMA ligand-imaging conjugates are administered locally or systemically, a wide range of permissible dosages are contemplated herein, including doses falling in the range from about 1 µg/kg to about 1 g/kg. In some embodiments, permissible dosages are contemplated herein in the units GBq, including doses falling in the range from about 2 GBq to about 13 GBq. The dosages may be single or divided, and may administered according to a wide variety of protocols, including q.d., b.i.d., t.i.d., or even every other day, biweekly (b.i.w.), once a week, once a month, once a quarter, and the like. In each of these cases it is understood that the therapeutically effective amounts described herein correspond to the instance of administration, or alternatively to the total daily, weekly, monthly, or quarterly dose, as determined by the dosing protocol. In some embodiments, the compound of the formula 1 can be administered once per week, or once every two weeks, or once every three weeks, or once every four weeks, or once every five weeks, or once every six weeks, or once every seven weeks, or once every eight weeks, and the like In one aspect, a Compound 1 or a PSMA ligand-imaging conjugate as described herein may be administered directly into the blood stream, into muscle, or into an internal organ. Suitable routes for such parenteral administration include intravenous, intraarterial, intraperitoneal, intrathecal, epidural, intracerebroventricular, intraurethral, intrasternal, intracranial, intratumoral, intramuscular and subcutaneous delivery. Suitable means for parenteral administration include needle (including microneedle) injectors, needle-free injectors and infusion techniques.

In one illustrative aspect, parenteral formulations are typically aqueous solutions which may contain carriers or excipients such as salts, carbohydrates and buffering agents (preferably at a pH of from 3 to 9), but, for some applications, they may be more suitably formulated as a sterile non-aqueous solution or as a dried form to be used in conjunction with a suitable vehicle such as sterile, pyrogen-free water. In other embodiments, any of the liquid formulations described herein may be adapted for parenteral administration of the Compound 1 or PSMA ligand-imaging conjugates described herein. The preparation of parenteral formulations under sterile conditions, for example, by lyophilization under sterile conditions, may readily be accomplished using standard pharmaceutical techniques well known to those skilled in the art. In one embodiment, the solubility of a Compound 1 or a PSMA ligand-imaging conjugate used in the preparation of a parenteral formulation may be increased by the use of appropriate formulation techniques, such as the incorporation of solubility-enhancing agents.

In various embodiments, formulations for parenteral administration may be formulated for immediate and/or modified release. In one illustrative aspect, active agents of the invention (i.e., the Compound 1 or PSMA ligand-imaging conjugates) may be administered in a time release formulation, for example in a composition which includes a slow release polymer. The active Compound 1 or PSMA ligand-imaging conjugates can be prepared with carriers that will protect the Compound 1 or PSMA ligand-imaging conjugate against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PGLA). Methods for the preparation of such formulations are generally known to those skilled in the art. In another embodiment, the Compound 1 or PSMA ligand-imaging conjugates described herein or compositions comprising the Compound 1 or PSMA ligand-imaging conjugates may be continuously administered, where appropriate.

In one embodiment, a kit is provided. If a combination of active Compound 1 and PSMA ligand-imaging conjugates is to be administered, two or more pharmaceutical compositions may be combined in the form of a kit suitable for sequential administration or co-administration of the compositions. Such a kit comprises two or more separate pharmaceutical compositions, at least one of which contains a Compound 1 or PSMA ligand-imaging conjugate described herein, and means for separately retaining the compositions, such as a container, divided bottle, or divided foil packet. In another embodiment, compositions comprising one or more of the Compound 1 or PSMA ligand-imaging conjugates described herein, in containers having labels that provide instructions for use of the Compound 1 or PSMA ligand-imaging conjugates for patient selection and/or treatment are provided.

In one embodiment, sterile injectable solutions can be prepared by incorporating the active agent in the required amount in an appropriate solvent with one or a combination of ingredients described above, as required, followed by filtered sterilization. Typically, dispersions are prepared by incorporating the active Compound 1 or PSMA ligand-imaging conjugate into a sterile vehicle which contains a dispersion medium and any additional ingredients of those described above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof, or the ingredients may be sterile-filtered together.

The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. In one embodiment, the proper fluidity can be maintained, for example, by the use of a coating such as lecithin, by the maintenance of the required particle size in the case of dispersion and by the use of surfactants.

Any effective regimen for administering Compound 1 can be used. For example, Compound 1 can be administered as single doses, or the doses can be divided and administered as a multiple-dose daily regimen. Further, a staggered regimen, for example, one to five days per week can be used as an alternative to daily treatment, and for the purpose of the methods described herein, such intermittent or staggered daily regimen is considered to be equivalent to every day treatment and is contemplated. In one illustrative embodiment the patient is treated with multiple injections of Compound 1 to treat the cancer. In one embodiment, the patient is injected multiple times (preferably about 2 up to about 50 times) with Compound 1, for example, at 12-72 hour intervals or at 48-72 hour intervals. Additional injections of Compound 1 can be administered to the patient at an interval of days or months after the initial injections(s) and the additional injections can prevent recurrence of the cancer.

Any suitable course of therapy with Compound 1 can be used. In one embodiment, individual doses and dosage regimens are selected to provide a total dose administered during a month of about 15 mg. In one illustrative example, Compound 1 is administered in a single daily dose administered five days a week, in weeks 1, 2, and 3 of each 4 week cycle, with no dose administered in week 4. In an alternative example, Compound 1 is administered in a single daily dose administered three days a week, of weeks 1, and 3 of each 4 week cycle, with no dose administered in weeks 2 and 4. In an alternative example, Compound 1 is administered biweekly on weeks 1 and 2, i.e. on days 1, 4, 8, 11, of a 3-week cycle. In an alternative example, Compound 1 is administered once weekly on weeks 1 and 2, i.e. days 1 and 8 of a 3-week cycle.

The unitary daily dosage of the Compound 1 can vary significantly depending on the patient condition, the cancer being treated, the route of administration of the Compound 1 and tissue distribution, and the possibility of co-usage of other therapeutic treatments, such as radiation therapy or additional drugs in combination therapies. The effective amount to be administered to a patient is based on body surface area, mass, and physician assessment of patient condition. Therapeutically effective doses (also referred to herein as "therapeutically effective amount") can range, for example, from about 0.5 mg/m$^2$ to about 10.0 mg/m$^2$. The therapeutically effective doses described herein also include ranges of about 0.5 mg/m$^2$ to about 9.5 mg/m$^2$, about 0.5 mg/m$^2$ to about 9.0 mg/m$^2$, about 0.5 mg/m$^2$ to about 8.5 mg/m$^2$, about 0.5 mg/m$^2$ to about 8.0 mg/m$^2$, about 0.5 mg/m$^2$ to about 7.5 mg/m$^2$, about 0.5 mg/m$^2$ to about 7.0 mg/m$^2$, about 0.5 mg/m$^2$ to about 6.5 mg/m$^2$, about 0.5 mg/m$^2$ to about 6.0 mg/m$^2$, about 0.5 mg/m$^2$ to about 5.5 mg/m$^2$, about 0.5 mg/m$^2$ to about 5.0 mg/m$^2$, about 0.5 mg/m$^2$ to about 4.5 mg/m$^2$, about 0.5 mg/m$^2$ to about 4.0 mg/m$^2$, about 0.5 mg/m$^2$ to about 3.5 mg/m$^2$, about 0.5 mg/m$^2$ to about 3.0 mg/m$^2$, about 0.5 mg/m$^2$ to about 2.5 mg/m$^2$, about 0.5 mg/m$^2$ to about 2.0 mg/m$^2$, about 0.5 mg/m$^2$ to about 1.5 mg/m$^2$, about 1.0 mg/m$^2$ to about 9.5 mg/m$^2$, about 1.0 mg/m$^2$ to about 9.0 mg/m$^2$, about 1.0 mg/m$^2$ to about 8.5 mg/m$^2$, about 1.0 mg/m$^2$ to about 8.0 mg/m$^2$, about 1.0 mg/m$^2$ to about 7.5 mg/m$^2$, about 1.0 mg/m$^2$ to about 7.0 mg/m$^2$, about 1.0 mg/m$^2$ to about 6.5 mg/m$^2$, about 1.0 mg/m$^2$ to about 6.0 mg/m$^2$, about 1.0 mg/m$^2$ to about 5.5 mg/m$^2$, about 1.0 mg/m$^2$ to about 5.0 mg/m$^2$, about 1.0 mg/m$^2$ to about 4.5 mg/m$^2$, about 1.0 mg/m$^2$ to about 4.0 mg/m$^2$, about 1.0 mg/m$^2$ to about 3.5 mg/m$^2$, about 1.0 mg/m$^2$ to about 3.0 mg/m$^2$, about 1.0 mg/m$^2$ to about 2.5 mg/m$^2$, about 1.0 mg/m$^2$ to about 2.0 mg/m$^2$, and about 1.0 mg/m$^2$ to about 1.5 mg/m$^2$. One of skill in the art will readily appreciate that the therapeutically effective dose may vary within the various ranges provided above based on the factors noted above. The therapeutically effective dose for any particular patient or group of patients may be any number value between about 0.5 mg/m$^2$ and about 10.0 mg/m$^2$, including but not limited to 1.0 mg/m$^2$, 1.5, mg/m$^2$, 2.0 mg/m$^2$, 2.5 mg/m$^2$, 3.0 mg/m$^2$, 3.5 mg/m$^2$, 4.0 mg/m$^2$, 4.5 mg/m$^2$, 5.0 mg/m$^2$, 5.5 mg/m$^2$, 6.0 mg/m$^2$, 6.5 mg/m$^2$, 7.0 mg/m$^2$, 7.5 mg/m$^2$, 8.0 mg/m$^2$, 8.5 mg/m$^2$, 9.0 mg/m$^2$, 9.5 mg/m$^2$ and 10.0 mg/m$^2$. The total dose may be administered in single or divided doses and may, at the physician's discretion, fall outside of the typical range given herein.

In some embodiments, the compound of the formula 1 can administered in combination with a second treatment. In some embodiments, the second treatment is best supportive treatment. In some embodiments, the second treatment is best standard of care treatment. In some embodiments, the second treatment is best supportive/best standard of care treatment. In some embodiments, the second treatment is an androgen axis systemic treatment. In some embodiments, the androgen axis systemic treatment is selected from the group consisting of abiraterone, orteronel, galeterone, sevit-eronel, apalutamide, enzalutamide, and combinations thereof. In some embodiments, the second treatment is radiation therapy. In some embodiments, the radiation therapy is external beam radiation therapy (EBRT).

The PSMA ligand-imaging conjugates and Compound 1 described herein may contain one or more chiral centers, or may otherwise be capable of existing as multiple stereoisomers. Accordingly, it is to be understood that the present invention includes pure stereoisomers as well as mixtures of stereoisomers, such as enantiomers, diastereomers, and enantiomerically or diastereomerically enriched mixtures. The PSMA ligand-imaging conjugates and Compound 1 described herein may be capable of existing as geometric isomers. Accordingly, it is to be understood that the present invention includes pure geometric isomers or mixtures of geometric isomers.

It is appreciated that the PSMA ligand-imaging conjugates and Compound 1 described herein may exist in unsolvated forms as well as solvated forms, including hydrated forms. In general, the solvated forms are equivalent to unsolvated forms and are encompassed within the scope of the present invention. The PSMA ligand-imaging conjugates and Compound 1 described herein may exist in multiple crystalline or amorphous forms. In general, all physical forms are equivalent for the uses contemplated by the present invention and are intended to be within the scope of the present invention.

In another embodiment, compositions and/or dosage forms for administration of Compound 1 are prepared from Compound 1 with a purity of at least about 90%, or about 95%, or about 96%, or about 97%, or about 98%, or about 99%, or about 99.5%. In another embodiment, compositions and or dosage forms for administration of Compound 1 are prepared from Compound 1 with a purity of at least 90%, or at least 95%, or at least 96%, or at least 97%, or at least 98%, or at least 99%, or at least 99.5%.

In another embodiment, compositions and/or dosage forms for administration of the PSMA ligand-imaging conjugate are prepared from the PSMA ligand-imaging conjugate with a purity of at least about 90%, or about 95%, or about 96%, or about 97%, or about 98%, or about 99%, or about 99.5%. In another embodiment, compositions and or dosage forms for administration of the PSMA ligand-imaging conjugate are prepared from the PSMA ligand-imaging conjugate with a purity of at least 90%, or at least 95%, or at least 97%, or at least 98%, or at least 99%, or at least 99.5%.

In another embodiment, compositions and/or dosage forms for administration of radiolabeled PSMA ligand-imaging conjugate are prepared from the PSMA ligand-imaging conjugate with a radiochemical purity of at least about 90%, or about 95%, or about 96%, or about 97%, or about 98%, or about 99%, or about 99.5%. In another embodiment, compositions and or dosage forms for administration of the PSMA ligand-imaging conjugate are prepared from the PSMA ligand-imaging conjugate with a purity of at least 90%, or at least 95%, or at least 96%, or at least 97%, or at least 98%, or at least 99%, or at least 99.5%.

The purity of Compound 1 or the PSMA ligand-imaging conjugates described herein may be measured using any conventional technique, including various chromatography or spectroscopic techniques, such as high pressure or high performance liquid chromatography (HPLC), nuclear magnetic resonance spectroscopy, TLC, UV absorbance spectroscopy, fluorescence spectroscopy, and the like.

In another embodiment, the Compound 1 or PSMA ligand-imaging conjugate described herein is provided in a sterile container or package.

In one aspect, a clinical benefit of the patient to treatment with Compound 1 can be characterized as overall survival (OS). As used herein, the term "overall survival (OS)" means the time from the date of randomization to the date of death from any cause.

In one aspect, a clinical benefit of the patient to treatment with Compound 1 can be characterized utilizing Response Evaluation Criteria in Solid Tumors (RECIST) criteria. Illustratively, the criteria have been adapted from the original *WHO Handbook* (3), taking into account the measurement of the longest diameter for all target lesions: complete response, (CR) —the disappearance of all target lesions; partial response (PR) —at least a 30% decrease in the sum of the longest diameter of target lesions, taking as reference the baseline sum longest diameter; stable disease (SD) —neither sufficient shrinkage to qualify for partial response nor sufficient increase to qualify for progressive disease, taking as reference the smallest sum longest diameter since the treatment started; progressive disease (PD) —at least a 20% increase in the sum of the longest diameter of target lesions, taking as reference the smallest sum longest diameter recorded since the treatment started or the appearance of one or more new lesions. In another aspect overall disease response rate (ORR) is a clinical benefit and is calculated as the percent of patients who achieve a best response of CR or PR. Overall disease control rate (DCR) can be another clinical benefit and is calculated as the percent of patients who achieve a best response of CR, PR, or SD. In some embodiments, the response can be disease control rate (DCR) as measured by RECIST v1.1 criteria.

In another aspect, a clinical benefit of the patient to treatment with Compound 1 can be characterized as radiographic progression-free survival (rPFS). As used herein, "radiographic progression-free survival (rPFS)" means the time from the date of randomization to the date of radiographic disease progression as outlined in Prostate Cancer Working Group 3 (PCWG3) Guidelines or death from any cause. See, for example, Scher H I, Morris M J, Stadler W M, Higano C, Basch E, Fizazi K, et al. Trial Design and Objectives for Castration-Resistant Prostate Cancer: Updated Recommendations from the Prostate Cancer Clinical Trials Work Group 3. J Clin Oncol 2016; 34(12):1402-18. In another aspect, a clinical benefit of the patient to treatment with Compound 1 can be characterized as time to a first symptomatic skeletal event (SSE). It will be appreciated that symptomatic skeletal event means a clinically significant pathological fracture, surgery or radiation to bone, or spinal cord compression. As used herein, "time to a first symptomatic skeletal event" means date of randomization to the date of first new symptomatic pathological bone fracture, spinal cord compression, tumor-related orthopedic surgical intervention, or requirement for radiation therapy to relieve bone pain, whichever occurs first.

In one illustrative example overall survival is the time to death for a given patient defined as the number of days from the first day the patient received protocol treatment (C1D1) to the date of the patient's death. All events of death can be included, regardless of whether the event occurred while the patient was still taking the study drug or after the patient discontinued the study drug. If a patient has not died, then the data can be censored at the last study visit, or the last contact date, or the date the patient was last known to be alive, whichever is last.

Alternatively, a clinical benefit of the patient as a result of treatment with Compound 1 can be characterized as inhibition of tumor growth which can be identified in a patient through, for example, follow-up imaging of the patient's cancer after treatment with Compound 1. For example, inhibition of tumor growth can be characterized by measuring the size of tumors in a patient after administration of Compound 1 according to any of the imaging techniques described herein, where the inhibition of tumor growth is indicated by a stable tumor size, or by a reduction in tumor size. It will be appreciated that the identification of inhibition of tumor growth can be accomplished using a variety of techniques, and is not limited to the imaging methods described herein (e.g CT, MRI, PET imaging, SPECT imaging or chest x-ray).

In one embodiment, a method is provided of determining whether Compound 1 is indicated for the treatment of a patient with cancer, the method comprising the step of determining the PSMA status in a patient with cancer wherein Compound 1 is indicated for the treatment of the patient if the PSMA status of the patient is positive.

In one embodiment, a method is provided of assessing whether Compound 1 is indicated for the treatment of a patient with one of the cancers described herein. The method comprises the steps of visually determining PSMA status in the patient wherein PSMA status is based on a imaging tumors that are PSMA positive in the patient, and wherein the Compound 1 is indicated for the treatment of the patient when the PSMA status of the patient is positive.

In the above-described embodiments, if a patient is in the group with positive PSMA status, a clinical benefit of Compound 1 treatment is indicated. In one embodiment, the clinical benefit to the patient can be overall survival of the patient, ability to receive four or more cycles of therapy with Compound 1, inhibition of tumor growth, stable disease, a partial response of the patient to therapy, a complete response of the patient to therapy, disease control (i.e., the best result obtained is a complete response, a partial response, or stable disease), and/or overall disease response (i.e., the best result obtained is a complete response or a partial response). In one illustrative example, the clinical benefit for a patient being treated for pleural mesothelioma or adenocarcinoma (e.g. adenocarcinoma of the gastroesophageal junction) is stable disease.

In another embodiment, the methods described herein include the following examples. The examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

EXAMPLES

Example 1

A. Design:

Patients with PSMA positive scans were randomized in a 2:1 ratio to receive either Compound 1 plus best supportive/best standard of care or to receive best supportive/best standard of care only. Best supportive/best standard of care was determined by the treating physician/investigator. The study is open-label and patients are monitored throughout the 6 to 10-month treatment period for survival, disease progression, and adverse events. A long-term follow-up period includes the collection of survival and treatment updates, adverse events assessment, as well as blood for hematology and chemistry testing. During follow-up, patients are contacted every 3 months (±1 month) via phone, email, or letter for 24 months or until the overall censoring rate for survival reduces to a level identified in the SAP.

B. Arm 1: Compound 1 Plus Best Supportive/Best Standard of Care (BS/BSOC)

Approximately 160 patients were randomized to receive the investigational product at a dose of 7.4 GBq (±10%) Compound 1 (dose is equivalent to 200 mCi) intravenously every 6 weeks (±1 week) for a maximum of 6 cycles, plus best supportive/best standard of care (BS/BSOC). After 4 cycles, patients are assessed for (1) evidence of response, (2) residual disease, and (3) tolerance to Compound 1. A saline flush with=10 mL of normal saline is administered to ensure patency of the intravenous line before administering with $^{177}$Lu-PSMA-617 administration. $^{177}$Lu-PSMA-617 was administered slowly by the intravenous route through an indwelling catheter and followed by a saline flush. The time of administration must be recorded. The total activity administered must be measured (GBq). To-date patients have received between 1-6 cycles in the randomized arm. To-date approximately 320 patients have been scanned with Ga-PSMA-imaging Conjugate 4.

C. Arm 2: Best Supportive/Best Standard of Care (BS/BSOC) Alone

Patients randomized to this are will receive best supportive/best standard of care (BS/BSOC) as determined by the investigator D. Outcome Measures:

Overall survival (OS) in patients with progressive PSMA-positive mCRPC who receive Compound 1 in addition to best supportive/standard of care.

What is claimed is:

1. A method for treating a cancer in a patient in need of such treatment comprising, administering to the patient a therapeutically effective amount of a composition comprising a compound of the formula 1

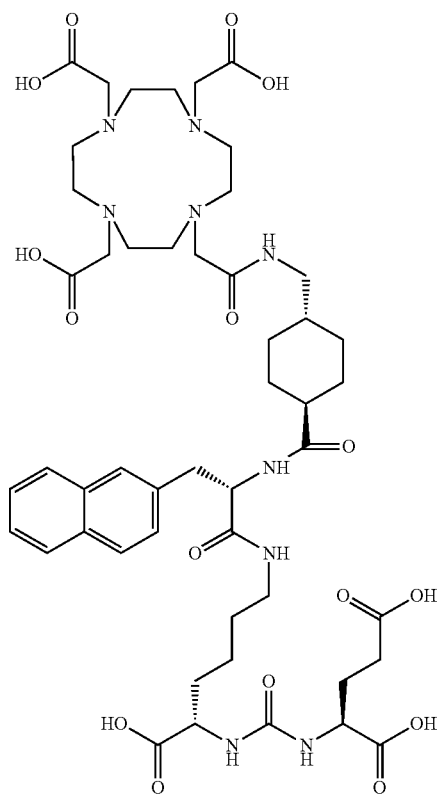

wherein the compound is complexed with Lu;
wherein the composition provides about 7.4 GBq of radioactivity per administration;
wherein the composition is administered on a schedule of once per every 4 to 6 weeks for 4 to 6 cycles,
wherein the cancer is metastatic castration-resistant prostate cancer, and
wherein the patient has been treated with a prior androgen axis systemic treatment.

2. The method of claim 1, wherein the composition is administered in a parenteral dosage form.

3. The method of claim 2, wherein the parenteral dosage form is selected from the group consisting of intradermal, subcutaneous, intramuscular, intraperitoneal, intravenous, and intrathecal.

4. The method of claim 3, further comprising imaging PSMA expression by the cancer.

5. The method of claim 4, wherein the imaging occurs before the step of administering.

6. The method of claim 5, wherein the imaging is performed by imaging and wherein the imaging is selected from the group consisting of SPECT imaging or PET imaging.

7. The method of claim 6, further comprising determining the PSMA status of the patient by imaging.

8. The method of claim 7, wherein the imaging in the step of determining is SPECT imaging.

9. The method of claim 8, wherein the PSMA status of the patient correlates with a clinical benefit to the patient selected from the group consisting of inhibition of tumor growth, stable disease, a partial response, and a complete response.

10. The method of claim 1, wherein the prior androgen axis systemic treatment is selected from the group consisting of abiraterone, orteronel, galeterone, seviteronel, apalutamide, enzalutamide, and combinations thereof.

11. The method of claim 10, wherein the patient has been treated with a prior treatment selected from the group consisting of chemotherapeutic agent, surgery, radiation therapy, immunotherapy, photodynamic therapy, stem cell therapy, and hyperthermia.

12. The method of claim 11, wherein the prior treatment is selected from the group consisting of palifosfamide, 5-fluorouracil, capecitabine, pemetrexed, cisplatin, carboplatin, gemcitabine, paclitaxel, vinorelbine, eribulin, docetaxel, cyclophosphamide, and doxorubicin, regorafinib.

13. The method of claim 1, wherein the composition is administered in combination with a second treatment.

14. The method of claim 13, wherein the second treatment is an androgen axis systemic treatment selected from the group consisting of abiraterone, orteronel, galeterone, seviteronel, apalutamide, enzalutamide, and combinations thereof.

15. The method of claim 13, wherein the second treatment is external beam radiation therapy (EBRT).

16. The method of claim 1, wherein the composition provides a total dose of about 29.6 to about 44 GBq of radioactivity.

17. A method for treating prostate cancer in a patient in need of such treatment comprising, administering to the patient a therapeutically effective amount of a composition comprising a compound of the formula 1

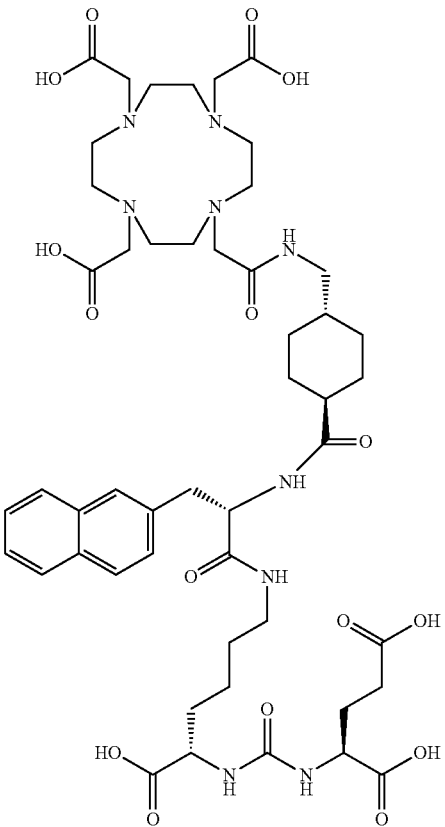

wherein the compound is complexed with $^{177}$Lu;

wherein the composition provides about 7.4 GBq of radioactivity per administration;

wherein the composition is administered on a schedule of once per every 4 to 6 weeks for 4 to 6 cycles such that the method provides a total dose of about 29.6 to about 44 GBq of radioactivity; and wherein the patient has been treated with at least one prior androgen axis systemic treatment.

* * * * *